United States Patent
Rico et al.

(10) Patent No.: US 8,361,409 B2
(45) Date of Patent: Jan. 29, 2013

(54) SYSTEMS AND METHODS FOR PRODUCING AQUEOUS SOLUTIONS AND GASES HAVING DISINFECTING PROPERTIES AND SUBSTANTIALLY ELIMINATING IMPURITIES

(75) Inventors: Bernardo N. Rico, Lewis Center, OH (US); James Liang-Hiong Chia, Columbus, OH (US); Margaret Emily Williams, Columbus, OH (US)

(73) Assignee: Odorstar Technology, LLC, Fort Lauderdale, FL (US)

( * ) Notice: Subject to any disclaimer, the term of this patent is extended or adjusted under 35 U.S.C. 154(b) by 884 days.

(21) Appl. No.: 12/067,451

(22) PCT Filed: Feb. 23, 2006

(86) PCT No.: PCT/US2006/006469
§ 371 (c)(1),
(2), (4) Date: Feb. 12, 2009

(87) PCT Pub. No.: WO2007/040588
PCT Pub. Date: Apr. 12, 2007

(65) Prior Publication Data
US 2009/0142235 A1    Jun. 4, 2009

(51) Int. Cl.
*A61L 9/00* (2006.01)
*B65B 31/00* (2006.01)
*C09K 3/00* (2006.01)
*B67D 5/00* (2006.01)
*C01B 7/00* (2006.01)
*B65D 81/24* (2006.01)

(52) U.S. Cl. ............ 422/305; 422/306; 53/432; 53/434; 43/125; 252/372; 252/380; 426/419; 426/124; 426/418; 99/467; 222/3; 222/94; 423/462; 206/205; 206/221; 206/219

(58) Field of Classification Search ............ 422/30–306; 53/432–434; 43/125; 252/372, 380; 426/419, 426/124, 418, 109, 120, 316, 319; 99/467; 222/3, 94; 423/462; 206/205, 221–222, 206/219
See application file for complete search history.

(56) References Cited

U.S. PATENT DOCUMENTS

| | | | |
|---|---|---|---|
| 2,022,262 A | 11/1935 | White | |
| 2,071,091 A | 2/1937 | Taylor | |
| 2,071,094 A | 2/1937 | Vincent | |
| 4,585,482 A | 4/1986 | Tice et al. | |
| 4,748,904 A * | 6/1988 | Razeto et al. | 99/467 |
| 5,023,012 A | 6/1991 | Buchan et al. | |
| 5,407,656 A | 4/1995 | Roozdar | |
| 6,046,243 A * | 4/2000 | Wellinghoff et al. | 514/772.3 |

(Continued)

FOREIGN PATENT DOCUMENTS
CA    959238    3/2008
WO    99/24356    5/1999

*Primary Examiner* — Jill Warden
*Assistant Examiner* — Monzer Chorbaji
(74) *Attorney, Agent, or Firm* — Christopher & Weisberg, P.A.

(57) ABSTRACT

A system for disinfecting and purifying aqueous solutions and water for drinking purposes comprising an outer pouch, a disinfectant generating device, and an inorganic coagulant. The disinfectant generating device is provided with a membrane shell defining at least two compartments which house a first reactant, a second reactant, and an inorganic coagulant. The disinfectant generating device is capable of producing a disinfectant when exposed to water or moisture and the disinfectant exits the compartment through the membrane shell. The inorganic coagulant aid the formation of flocs of the suspended dispersed particles in the aqueous solution.

9 Claims, 13 Drawing Sheets

U.S. PATENT DOCUMENTS

| | | |
|---|---|---|
| 6,063,425 A | 5/2000 | Kross et al. |
| 6,764,661 B1 * | 7/2004 | Girard .......................... 422/305 |
| 2,482,891 A1 | 3/2008 | Aston |

\* cited by examiner

SYSTEMS AND METHODS FOR PRODUCING AQUEOUS SOLUTIONS AND GASES HAVING DISINFECTING PROPERTIES AND SUBSTANTIALLY ELIMINATING IMPURITIES

CROSS REFERENCE TO RELATED APPLICATIONS

This application claims priority under 35 U.S.C. §365(a) to International Patent Application No. PCT/US2006/06469, filed Feb. 23, 2006, and under 35 U.S.C. §120 to International Patent Application No. PCT/US2006/06469, filed Feb. 23, 2006, which claims priority to U.S. patent application Ser. No. 11/229,758, filed Sep. 19, 2005.

FIELD OF THE INVENTION

The present invention relates generally to systems and methods for producing disinfectants and substantially eliminating impurities, and particularly to systems that produce a disinfectant when exposed to water or ambient moisture.

BACKGROUND OF THE INVENTION

Chlorine dioxide ($ClO_2$) is a relatively small, volatile, and versatile free radical molecule with bleaching, oxidizing, and deodorizing properties, as well as antimicrobial properties, namely, bactericidal, viricidal, sporicidal, algicidal, and fungicidal properties. It is frequently used to control microorganisms on or around food products because chlorine dioxide destroys the microorganisms without producing concentrations of byproducts that would pose a significant adverse risk to human health. Examples of these adverse byproducts that may be produced by other types of oxidants include chloramines and chlorinated organic compounds. Chlorine dioxide's physiological mode of destroying microbes has been attributed to the destruction of cell walls and cell membranes and disrupting transport of nutrients from the external environment into microorganisms.

Chlorine dioxide has also long been recognized for treatment and reduction of odors caused by compounds and microorganisms through an oxidation process. Examples of odor-causing compounds include: sulfur-containing compounds (hydrogen sulfide, mercaptan sulfides, organic disulfide, sulfoxides, etc.), oxygen containing compounds (phenols, aldehydes, aliphatic alcohols, etc.) and some nitrogen containing compounds (tertiary and secondary amines, etc.). A low concentration of chlorine dioxide, in either gaseous or liquid state, is effective for most antimicrobial and deodorization applications. In addition to chlorine dioxide, other compounds, such as peracetic acid, bromine, sulfur dioxide, and carbon dioxide also exhibit antimicrobial and disinfecting properties.

As an oxidizing biocide, chlorine dioxide can also be used as a disinfectant or as an oxidant in water treatment systems. It may be used in both the pre-oxidation and the post-oxidation stages of the treatment as a primary oxidant or as a primary or secondary disinfectant. By adding chlorine dioxide in the pre-oxidation phase of the purification of surface water, the growth of bacteria and algae can be controlled in the subsequent phases of the treatment. Chlorine dioxide also acts as an oxidant to the colloidal substances, aiding in the coagulation process and improving the removal of turbidity.

In its vapor state, chlorine dioxide is not stable during storage and can be explosive at concentrations above about 10% in dry air. At temperatures lower than −40° C., chlorine dioxide vapor can be compressed to a liquid state to reduce the risk of explosion; above this temperature, however, highly concentrated liquid chlorine dioxide can be explosive. Therefore, chlorine dioxide vapor or liquid is usually not produced and shipped under pressure. Instead, chlorine dioxide is typically generated at the point of use via conventional chlorine dioxide generators or other means. Conventional chlorine dioxide generation can be carried out in an efficient manner for large-scale operations to produce chlorine dioxide by reacting sodium chlorite or sodium chlorate solution with an acid such as sulfuric acid, hydrochloric acid, or a reducing agent. Chlorine dioxide can also be generated by one of the following reactions: mixing sodium chlorite solution with a strong chlorine solution at low pH, mixing a sodium chlorite solution with chlorine gas at near neutral pH under a vacuum, or reacting solid sodium chlorite in a sealed reactor cartridge with humidified chlorine gas flowing through it. All of the processes mentioned above require expensive generation equipment, high maintenance costs, and highly trained and skilled workers to operate the equipment in a safe manner. As a result, the use of such generators has been limited to the fields of poultry processing, pulp and paper bleaching, and water treatment facilities, where the high capital and operating cost of the generators can be justified by the large consumption of chlorine dioxide.

In addition to the methods discussed above, chlorine dioxide can also be generated by the electrolysis of sodium chlorite solutions. This process requires electricity to operate the electrolytic equipment, and high maintenance efforts to ensure the efficiency of the equipment. The electrolysis process not only produces less chlorine dioxide compared to conventional generators, but special sodium chlorite solutions are also required for this process to reduce the level of suspended solids and scaling that can clog the electrolytic cell. Further, proportional amount of wastes, such as sodium hydroxide solution, are produced along with chlorine dioxide during the electrolytic reaction.

A solution of a metal chlorite and water where the pH of the solution is maintained at 8 or above is sometimes referred to as a "stabilized chlorine dioxide" solution. Applications requiring small quantities of chlorine dioxide can be approached by the use of "stabilized chlorine dioxide", which generally refers to sodium chlorite, a reactant of chlorine dioxide. Sodium chlorite by itself only has bacteriostatic properties (inhibits rather than killing bacteria) and does not provide complete disinfection. Some claims have been made to the use of sodium chlorite as a bactericide in situations in which bacteria can provide the necessary acidity for the "activation" step to produce chlorine dioxide. In any case, the amount of chlorine dioxide produced under these conditions is insignificant. In most other cases, "stabilized chlorine dioxide" still requires the activation step of reacting a sodium chlorite solution with an acid. The pH of the reacting solution must be lowered to below 5, typically to a pH range between about 2 to about 3, in order to produce chlorine dioxide according to the following equation:

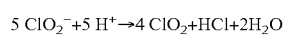

$$5\ ClO_2^- + 5\ H^+ \rightarrow 4\ ClO_2 + HCl + 2H_2O$$

This approach, or any other type of "two-part system," is usually performed at the application site, requiring trained personnel to properly activate the product. In addition, the use of "stabilized chlorine dioxide" requires mixing equipment and manipulation of potentially dangerous acids, thus exposing users to inadvertent skin contact and inhalation of acid vapors. Transportation of the "stabilized chlorine dioxide" also involves large volumes of water, resulting in a costly and difficult operation for remote and/or disaster recovery uses.

Attempts have also been made to manufacture devices that produce chlorine dioxide using a mixture of solid sodium chlorite and acidulant in solid forms (e.g. citric acid, sodium bisulfate, organic anhydride, etc.). These devices usually require complicated formulation processes, one of which involves drying individual reactants to lower their water content and mixing the dried reactants in the presence of desiccant materials (e.g. calcium chloride), to prevent the premature generation of chlorine dioxide that is initiated by atmospheric moisture. Such processes must take place in specially-designed environments that minimize moisture contact with mixed reactants during the formulation/packaging process. In addition, a protective barrier is required to prevent the contact of atmospheric moisture with the mixed reactants prior to use. In the presence of water/moisture, these devices generate chlorine dioxide solution or chlorine dioxide vapor. Due to the nature of the manufacturing process, these devices usually involve high manufacturing costs.

Many compositions and methods for generating chlorine dioxide solutions are known in the art. For example, U.S. Pat. No. 2,022,262 discloses stable stain-removing compositions made from a dry mixture of water-soluble alkaline chlorite salt, an oxalate, and an acid. U.S. Pat. No. 2,071,091 discloses the use of chlorous acid and chlorites to kill fungi and bacterial organisms by exposing the organisms to the compounds at a pH of less than about 7. The patent also discloses using dry mixtures of chlorites and acids to produce stable aqueous solutions useful as bleaching agents. U.S. Pat. No. 2,482,891 discloses stable, solid, substantially anhydrous compositions comprising alkaline chlorite salts and organic acid anhydrides, which release chlorine dioxide when contacted with water. U.S. Pat. No. 2,071,094 discloses deodorizing compositions in the form of dry briquettes formed of a mixture of soluble chlorite, an acidifying agent, and a filler of relatively low solubility. Chlorine dioxide is generated when the briquettes contact water. U.S. Pat. No. 4,585,482 discloses a long-acting biocidal composition comprising a microencapsulated mixture of chlorite and acid that when added to water releases chlorine dioxide. The primary purpose of the microencapsulation is to provide for hard particles that will be free flowing when handled. The microencapsulated composition also protects against water loss from the interior of the microcapsule. The microcapsules produce chlorine dioxide when immersed in water. The microcapsules release chlorine dioxide relatively slowly and are therefore not suitable for applications that require the preparation of chlorine dioxide on a relatively fast basis. U.S. Pat. No. 6,063,425 discloses a method for disinfecting a meat carcass by spray application of an aqueous solution containing from about 0.05 to 0.12% of a metal chlorite and a sufficient quantity of an acid having a pKa of from about 2.0 to 4.4 to adjust the pH of the aqueous solution to about 2.2-4.5. This adjustment helps to maintain the chlorite ion concentration in the form of chlorous acid to not more than about 35% by weight of the aqueous solution, the molar ratio of the acid to metal chlorite being at least equal to the first pKa of the acid multiplied by the grams/liter concentration of metal chlorite in the aqueous solution.

Many devices and methods for producing chlorine dioxide solution are also known in the art. For example, Canadian Patent No. 959,238 discloses using two water-soluble envelopes, one containing sodium chlorite and the other containing an acid, to generate chlorine dioxide solution. The envelopes are placed in water and the sodium chlorite and acid dissolve in the water and react to produce a chlorine dioxide solution. PCT Application PCT/US98/22564 (WO 99/24356) discloses a method and device for producing chlorine dioxide solutions wherein sodium chlorite and an acid are mixed and enclosed in a semi-permeable membrane device. When the device is placed in water, water penetrates the membrane. The acid and sodium chlorite dissolve in the water and react to produce chlorine dioxide. The chlorine dioxide exits the device through the membrane into the water in which the device is immersed producing a chlorine dioxide solution that can be used as an anti-microbial solution or for other purposes. The primary disadvantage of the disclosed device and method is that ambient moisture can penetrate the semi-permeable membrane and initiate the reaction prematurely.

In general, the above prior art devices and methods using membranes are susceptible to premature activation by water or water vapor and therefore have a reduced shelf life unless sufficient steps are taken to protect the devices from exposure to ambient moisture or water. In addition, such devices and methods are typically slow to interact with water and produce the desired chlorine dioxide.

U.S. Pat. No. 6,764,661 discloses a device for producing an aqueous chlorine dioxide solution when placed in water that solves the aforementioned problem. One of the advantages of this device is that it is not susceptible to activation by ambient moisture. The device includes a membrane shell that defines a compartment, which includes one or more dry reactants (e.g., a metal chlorite and an acid) capable of producing chlorine dioxide when exposed to water. The device is provided with wick means extending between the outer membranes, creating two inner compartments. The wick means absorb water and transport it into the compartment by capillary action. Once water has entered the inner compartments, the reactant(s) in the compartments dissolve in the water and produce chlorine dioxide in an aqueous solution. This device is generally used to produce an aqueous solution, having antimicrobial and disinfecting properties, when exposed to water. It is not designed to produce a vapor having antimicrobial and disinfecting properties.

In some water treatment operations, the process of coagulation is employed to separate suspended solids from water. In general, finely dispersed solids (colloids) suspended in water are stabilized by negative electric charges on their surfaces, causing them to repel each other. This repulsion prevents the colloids from colliding and forming larger masses, called "flocs". Coagulation promotes the aggregation of these colloidal particles to form flocs by destabilizing their surface charges. For example, cationic coagulants bond to negatively charged particles, thus lowering the charge and energy required to bring the colloidal particles into contact. As a result, the particles collide and form flocs.

Flocculation is the action of forming bridges between the flocs and binding the flocs into large agglomerates or clumps. Bridging occurs when segments of polymer chains of the flocs adsorb onto different particles, causing the flocs to aggregate. An anionic flocculant will react against a positively charged suspension, adsorbing on the particles and causing destabilization either by bridging or charge neutralization. Once suspended flocs are flocculated into larger flocs, they can usually be removed from the liquid by sedimentation, provided that a sufficient density difference exists between the suspended flocs and the liquid. The flocs can also be removed or separated by media filtration, straining, sedimentation, or floatation. Flocculation not only increases the size of the floc particles, but it also affects the physical nature of the flocs, making these particles less gelatinous and thereby easier to remove.

U.S. Pat. No. 5,023,012 discloses a composition for the purification of water, including a suitable coagulant for coagulating solid impurities dispersed in the water to form flocs and an organic hydrophilic colloid capable, when dispersed in the water, of absorbing large quantities of water to form a sol for aggregating the flocs. The proportion of organic hydrophilic colloid in the composition is such that when the composition is used to purify the intended quantity of water, the organic hydrophilic colloid does not interfere with coagulant dispersal in the water or with floc formation.

The aforementioned coagulating and purifying invention uses chlorine as a disinfectant. Recently, concern over the disinfection byproducts of chlorine has led to increased use of alternative disinfectants that produce safer byproducts. Chlorine reacts with organic matter in water to form trihalomethanes (THMs) and haloacetic acids (HAAs) which have been found to be carcinogenic.

The present invention provides systems and methods for disinfection and purification that overcome the aforementioned disadvantages and problems.

SUMMARY OF THE INVENTION

A system is provided for producing disinfectants and substantially eliminating impurities upon exposure of the system to water or moisture. In one embodiment, the inventive system is provided with a protective outer pouch that contains a disinfectant generating device for disinfecting water or aqueous solutions and substantially eliminating microbial contaminants and at least one inorganic coagulant for substantially removing impurities in water or the aqueous solutions. The disinfectant generating device comprises at least two dry reactants, in "powder" form or "tablet" form, capable of reacting and producing a disinfectant upon exposure of the device to water or ambient moisture. Examples of "powder" form include, but are not limited to: powders, granules, pellets, tablets, agglomerates, and the like. The inorganic coagulant is generally stored within the outer pouch, being outside of and separated from the disinfectant generating device. Alternatively, the inorganic coagulant may be stored within the disinfectant generating device.

In addition to the outer pouch, the disinfectant generating device, and the inorganic coagulant, the inventive system may additionally include at least one polymeric coagulant for aiding flocculation of impurities in water or aqueous solutions. Alternatively, the inventive system may include an outer pouch, a disinfectant generating device, at least one inorganic coagulant, and at least one organic hydrophilic colloid to aid the flocculation of the impurities. In yet another alternative, the inventive system may include an outer pouch, a disinfectant generating device, at least one inorganic coagulant, at least one polymeric coagulant, and at least one organic hydrophilic colloid. In still another embodiment, the inventive system may include an outer pouch, a disinfectant generating device containing at least two dry reactants, at least one surfactant, at least one fragrance material, at least one additive, or combinations thereof, at least one inorganic coagulant, and optionally at least one polymeric coagulant, at least one organic hydrophilic colloid, or a combination of the polymeric coagulant and the hydrophilic colloid. Alternatively, the at least one surfactant, the at least one fragrance material, and the at least one additive may be stored outside of and separated from the disinfectant generating device.

The disinfectant generating device comprises a membrane shell defining at least two compartments, and each compartment includes at least one dry reactant capable of reacting and producing a disinfectant upon exposure of the device to water or ambient moisture. Each compartment is provided with an outer membrane defining walls of the device and a wick means or an inner membrane providing physical separation of the dry reactants. Each of the at least two compartments may additionally include at least one inorganic coagulant, at least one polymeric coagulant, at least one organic hydrophilic colloid, or combinations thereof. Wick means or the inner membrane is provided in connection with the membrane shell and extends into one or both compartments for absorbing water or moisture and transporting water or moisture into at least one of the compartments, facilitating the reaction and producing a disinfectant in the compartment, and the disinfectant exits the compartment through the membrane shell.

In another embodiment of the disinfectant generating device, the device may additionally be provided with at least one water soluble membrane. The water-soluble membrane is sealed substantially continuously along the edges to one of the outer membranes of the device, for example, using a mechanical heat-sealing process, to form a third compartment of the device. Alternatively, the device may additionally be provided with at least two water soluble membranes and each of the at least two water soluble membranes is sealed substantially continuously to one of the outer membranes of the device along the edges to form a third compartment and a fourth compartment of the device. The third compartment and the fourth compartment may each contain at least one inorganic coagulant, at least one polymeric coagulant, at least one organic hydrophilic colloid, at least one surfactant, at least one fragrance material, at least one additive, or combinations thereof.

The at least two dry reactants, under reaction conditions, generate a disinfectant such as chlorine dioxide, peracetic acid, bromine, sulfur dioxide, carbon dioxide, and the like. In one embodiment, in which disinfectant generated in the device is chlorine dioxide, the first compartment of the device includes a metal chlorite component and the second compartment includes an acid component.

In an alternative embodiment of the inventive system, the system is provided with a package comprising a protective outer pouch and at least one tablet having disinfectant properties being stored within the outer pouch. The at least one disinfectant tablet may contain at least two dry reactants, at least one inorganic coagulant, at least one polymeric coagulant, at least one organic hydrophilic colloid, or a combination of the polymeric coagulant and the organic hydrophilic colloid. The disinfectant tablet may additionally contain at least one surfactant, at least one fragrance material, an additive, or a combination thereof. Upon use, the disinfectant tablet may be removed from the outer pouch and submerged in water or aqueous solutions for generating a disinfectant and substantially eliminating impurities in the water or aqueous solutions. Alternatively, the outer pouch may be constructed of a water soluble material and the entire package may be submerged in water or aqueous solutions upon use.

To disinfect and remove impurities from water and aqueous solutions, the elements of the inventive system are immersed in and added to water or an aqueous solution, and the water or solution is stirred and allowed to settle. The disinfectant generating device and the disinfectant tablet serve to substantially eliminate microbial contaminants in the water or solution; the inorganic coagulant promotes the aggregation of the solid impurities to form flocs; the polymeric coagulant and organic hydrophilic colloid aid in flocculation and clarification of a solution to be treated; and the surfactant helps the removal of soil from the solution to be treated or a surface and the reduction of surface tension of the solution to be treated.

In an embodiment where the inventive system is provided with a disinfectant generating device or a disinfectant tablet containing first and second reactants, an inorganic coagulant, and optionally a polymeric coagulant, an organic hydrophilic colloid, a surfactant, a fragrance material, an additive, or combinations thereof, the disinfection and purification process is commenced by opening the outer pouch of the system and placing the disinfectant generating device or the disinfectant tablet into a vessel, or the like, containing a predetermined volume of water or an aqueous solution. To promote dispersal of disinfectant and the coagulant(s), the aqueous solution is stirred and then allowed to settle, after which, the solution may be decanted and then filtered to remove the impurities.

In another embodiment where an inorganic coagulant, a polymeric coagulant, an organic hydrophilic colloid, a surfactant, a fragrance material, an additive, or combinations thereof are stored independently from the disinfectant generating device or disinfectant tablet, the inorganic coagulant, the polymeric coagulant, the organic hydrophilic colloid, the surfactant, the fragrance material, the additive, or combinations thereof are first added to the vessel of water or an aqueous solution. The aqueous solution is stirred to allow floes to form. The solution is then allowed to settle, after which, the disinfectant generating device or disinfectant tablet is placed in the aqueous solution.

For the generation of vapor or gases having disinfectant properties, the inventive system comprises a disinfectant vapor generating device for producing vapor having disinfectant properties upon exposure of the device to ambient moisture. The device is capable of providing sustained generation of vapor having disinfectant properties over a long period of time (weeks to months). The device is provided with an inner membrane that is sealed to at least outer membranes continuously or non-continuously along the edges of the device, via a mechanical heat sealing process, to form at least two compartments of the device and each of the at least two compartment contains at least one dry reactant and optionally at one deliquescent material. The inner membrane physically separates the dry reactants and is capable of absorbing and transporting small amounts of one of the partially dissolved reactants across the inner membrane to react with the other reactant in a separate compartment. When the device is exposed to the environment, the ambient moisture penetrates the outer membranes. The dry reactants then become hydrated and slowly dissolve. The partially dissolved reactants come into contact with each other across the inner membrane to produce a disinfectant vapor. Eventually, the generated disinfectant vapor slowly diffuses out of the outer membranes into the surrounding environment.

In another embodiment, the disinfectant vapor generating device comprises an inner membrane and two outer membranes, which are sealed together non-continuously along the edges of the device, to form a pouch having a plurality of small openings along the edges of the device for facilitating passage of moisture into the device. The small openings or gaps may be mechanically compressed to prevent the reactants from falling out from the device. These small openings increase the moisture transfer rate into the device, the reactants' dissolution rate, the rate of generation of the disinfectant vapor generation, as well as the rate of facilitating the passage of disinfectant vapor out of the device.

BRIEF DESCRIPTION OF THE DRAWINGS

Preferred embodiments of the present invention are described in detail below and illustrated in the drawings, in which.

DETAILED DESCRIPTION OF THE INVENTION

A system is provided for the production of disinfectants and substantially eliminating microbial contaminants, such as bacteria, viruses, and parasites, as well as removal of impurities upon exposure to water or moisture. In one embodiment, the inventive system is provided with a protective outer pouch, a disinfectant generating device including at least two dry reactants for the production of a disinfectant, and at least one inorganic coagulant for removing impurities in water or other aqueous solutions. In addition to the disinfectant generating device and the inorganic coagulant, the system may optionally be provided with at least one polymeric coagulant, at least one organic hydrophilic colloid, or a combination of the at least one polymeric coagulant and at least one organic hydrophilic colloid for aiding flocculation of the impurities in water or aqueous solutions. The inventive system may additionally be provided with at least one surfactant, a fragrance material, an additive, or a combination thereof. The disinfectant generating device, which will be described in further details below, may be in a configuration defined by at least two compartments and each compartment includes at least one dry reactant for producing a disinfectant. The disinfectant generating device may be further provided with at least one water soluble membrane sealed continuously to an outer membrane of the device along its edges to form a third compartment of the device. The dry reactants, the inorganic coagulant, the polymeric coagulant, the organic hydrophilic colloid, the surfactant, the fragrance material, the addictive, and combinations thereof may be in "powder" form or "tablet" form. As used herein and in the claims, the term "powder form" means components in a stable, solid, substantially anhydrous form that include, but are not limited to: powders, granules, pellets, tablets, agglomerates, and the like. The disinfectant produced by the inventive system may include, but is not limited to, chlorine dioxide, peracetic acid, chlorous acid, bromine, and the like.

In another embodiment of the inventive system, the system is provided with an outer pouch and at least one disinfectant generating tablet for producing a disinfectant. The tablet may contain at least two dry reactants, at least one inorganic coagulant, at least one polymeric coagulant, at least one organic hydrophilic colloid, at least one surfactant, at least one fragrance material, an additive, or combinations thereof.

Figure 1:
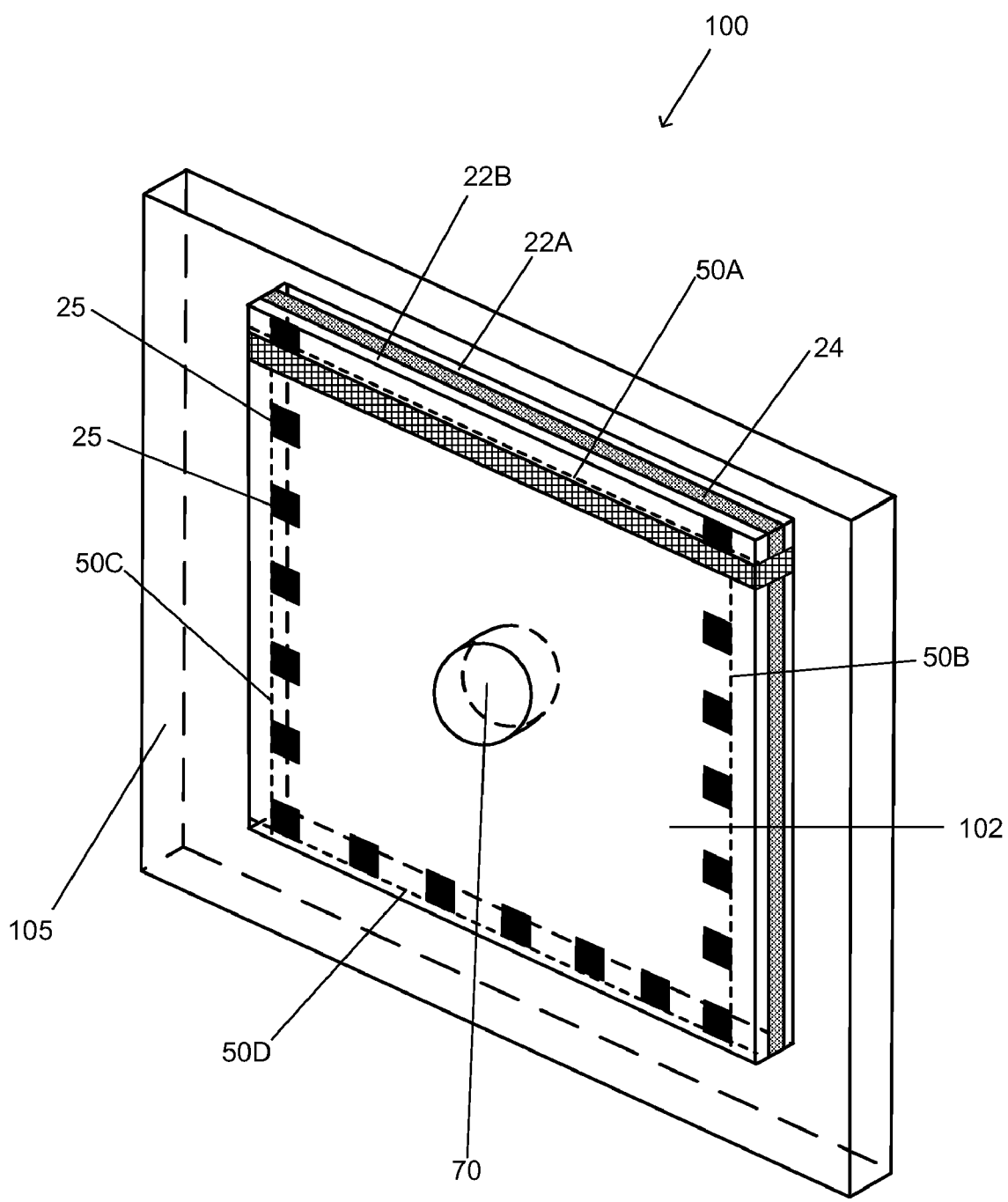
FIG. 1 shows a front perspective view of an embodiment of the inventive system, having an outer pouch that contains a disinfectant generating device.

FIG. 1 shows inventive system 100 comprising a package having a sealed or sealable outer pouch 105 that contains a disinfectant generating device 102. The outer pouch 105 may be constructed of a lightweight, strong, vapor-impermeable, water-soluble, and tear and abrasion-resistant material such as, but is not limited to, aluminum, aluminum foil, polyethylene, polyvinyl alcohol, and the like, and combinations thereof.

Figure 2:
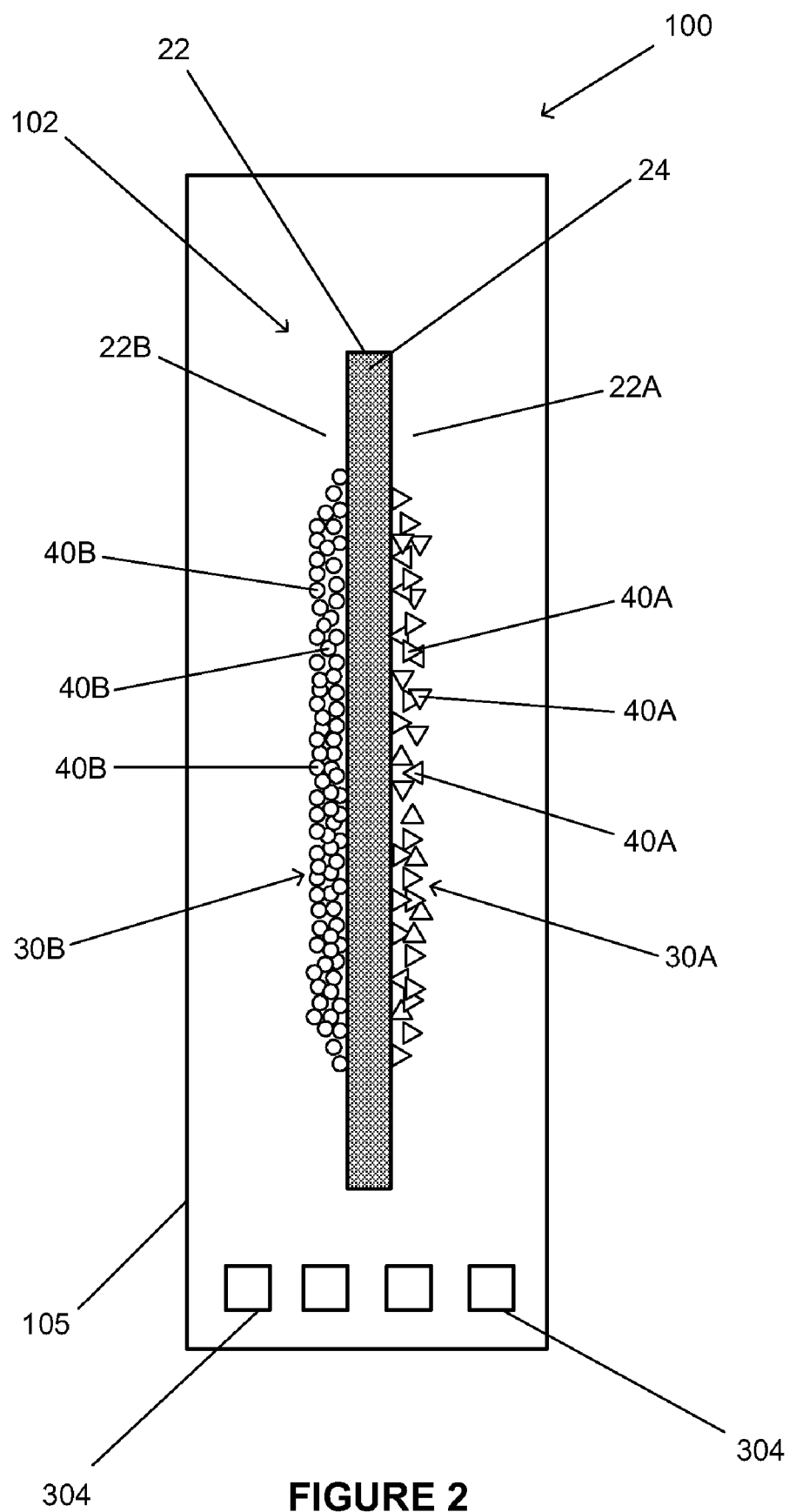
FIG. 2 shows a cross-sectional view of another embodiment of the inventive system, illustrating an outer pouch containing a disinfectant generating device and an inorganic coagulant stored outside of the disinfectant generating device in the outer pouch.
Figure 4:
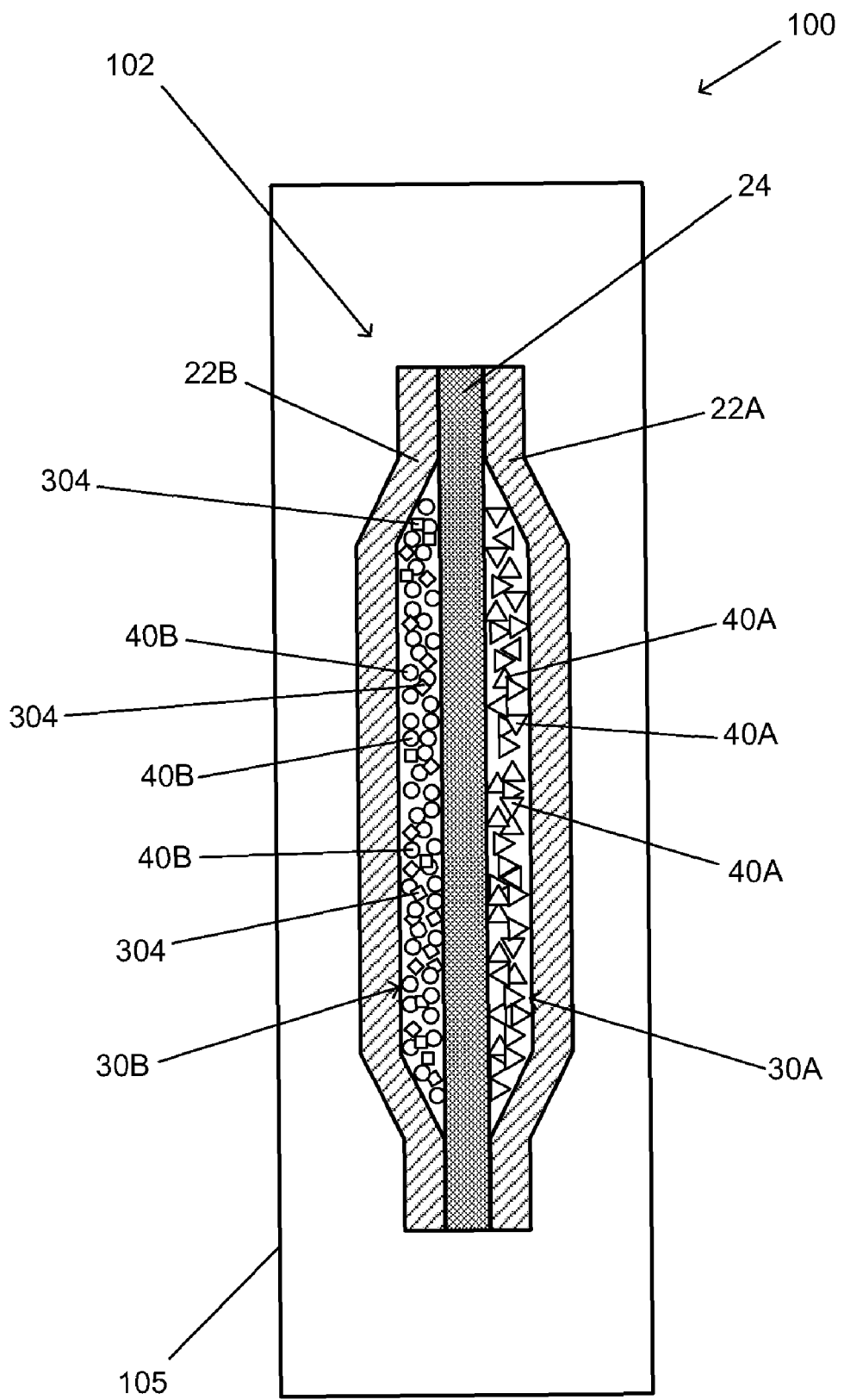
FIG. 4 shows a cross-sectional view of still another embodiment of the inventive system, illustrating an outer pouch containing a disinfectant generating device, and an inorganic coagulant stored inside of the disinfectant generating device.

In one embodiment of the inventive system 100, shown in FIG. 2, a disinfectant generating device 102 and at least one inorganic coagulant 304 are stored in outer pouch 105 of system 100. The disinfectant generating device 102, for example, is provided with at least two compartments 30A, 30B and each compartment 30A, 30B contains a first dry reactant 40A and a second dry reactant 40B in powder form capable of producing a biocide or disinfectant when the reactants 40A, 40B react with water or moisture. Inorganic coagulant 304 may include, but is not limited to, ferric sulfate, ferric chloride, ferrous sulfate, aluminum sulfate, polyaluminum chloride, sodium aluminate, chlorinated copper, and the like. In the embodiment shown in FIG. 2, inorganic coagulant 304 may be stored in outer pouch 105 and outside of and separated from disinfectant generating device 102. Alternatively, as shown in FIG. 4, inorganic coagulant 304 may be stored inside of compartments 30A, 30B of disinfectant generating device 102. In one embodiment, inventive system 100 contains approximately between 0-90% by mass first dry reactant 40A, approximately between 0-90% by mass second dry reactant 40B, and approximately between 0-40% by mass inorganic coagulant 304. In another embodiment, system 100 contains approximately between 10-50% by mass of each of the first and second dry reactants 40A, 40B and approximately between 0-40% by mass of inorganic coagulant 304.

Figure 3:
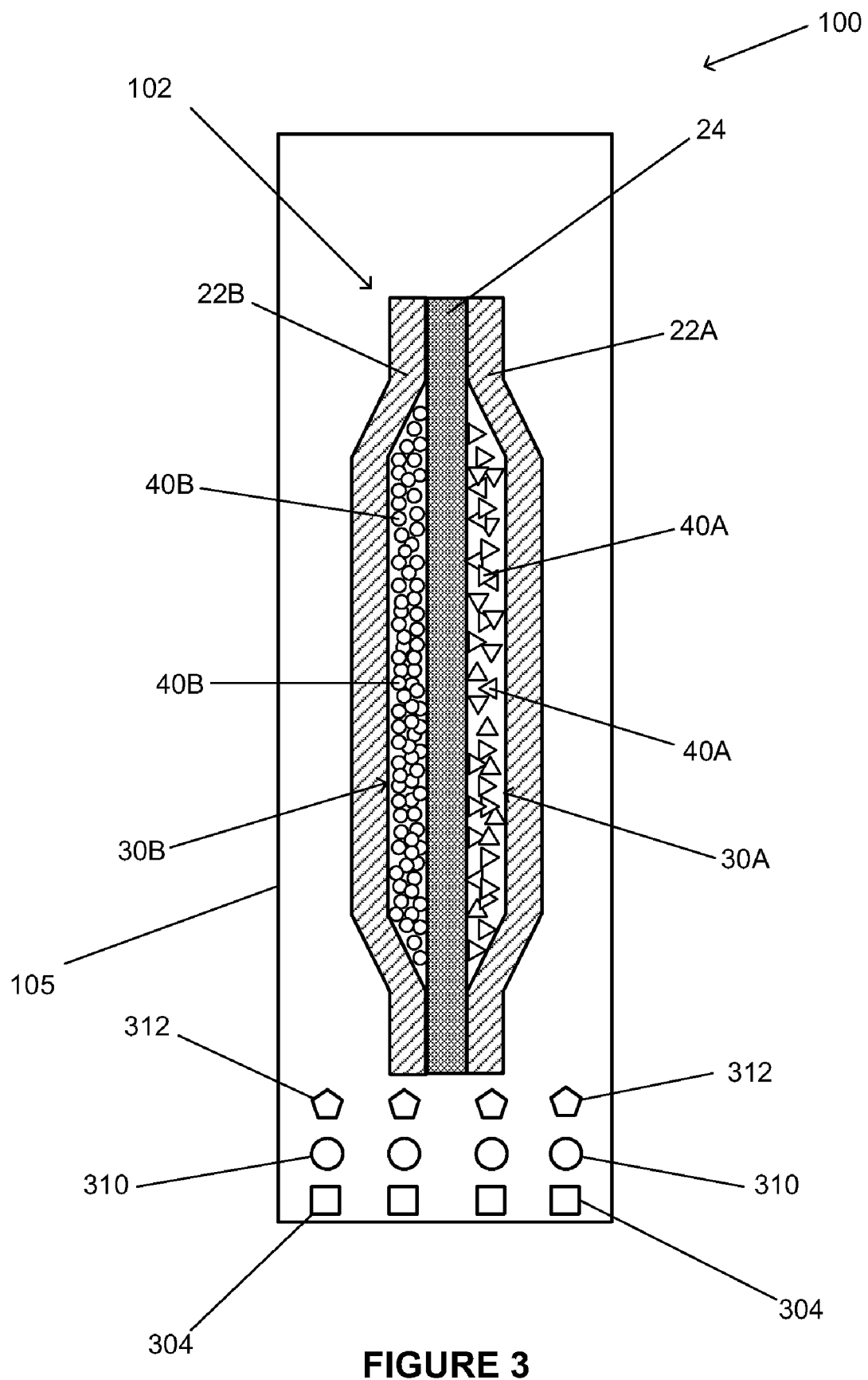
FIG. 3 shows a cross-sectional view of yet another embodiment of the inventive system, illustrating an outer pouch containing a disinfectant generating device, and an inorganic coagulant, a polymeric coagulant, and an organic hydrophilic colloid stored outside of the disinfectant generating device in the outer pouch.

FIG. 3 shows another embodiment of inventive system 100 provided with outer pouch 105 containing a disinfectant generating device 102 including a first dry reactant 40A and a second dry reactant 40B, and a mixture of at least one inorganic coagulant 304 and at least one polymeric coagulant 310 stored outside of and separated from device 102. Alternatively, the mixture of inorganic coagulant 304 and polymeric coagulant 310 may be stored inside of compartments 30A, 30B of disinfectant generating device 102. In another alternative, inorganic coagulant 304 may be stored inside of device 102 and polymeric coagulant 310 may be stored outside of device 102. In yet another alternative, polymeric coagulant 310 may be stored inside of device 102 and inorganic coagulant 304 may be stored outside of device 102. Polymeric coagulant 310 may include, but is not limited to, cationic polyelectrolytes, polyDADMAC, epiDMA, and anionic and nonionic polyelctrolytes such as polyacrylamide polymers, copolymers, and terpolymers. Organic polymers such as the water extract, *Moringa oleifera*, and chitin can also be used as polymeric coagulant 310. In one embodiment, inventive system 100 contains approximately between 0-90% by mass first dry reactant 40A, approximately between 0-90% by mass second dry reactant 40B, approximately between 0-40% by mass inorganic coagulant 304, and approximately between 0-40% polymeric coagulant 310. In another embodiment, system 100 contains approximately between 10-50% by mass of each of the first and second dry reactants 40A, 40B, approximately between 0-40% by mass of the inorganic coagulant, and approximately between 0-40% by mass polymeric coagulant 310.

In another embodiment, as illustrated by FIG. 3, outer pouch 105 of system 100 contains a disinfectant generating device 102 having a first dry reactant 40A and a second dry reactant 40B, a mixture of at least one inorganic coagulant 304 and at least one organic hydrophilic colloid 312 stored outside of and separated from disinfectant generating device 102. Alternatively, the mixture of inorganic coagulant 304 and organic hydrophilic colloid 312 may be stored inside of device 102. In another alternative, inorganic coagulant 304 may be stored inside of device 102 and organic hydrophilic colloid 312 may be stored outside of device 102. In yet another alternative, organic hydrophilic colloid 312 may be stored inside of device 102 and inorganic coagulant 304 may be stored outside of device 102. Hydrophilic colloid 312 may include, but is not limited to, activated silica and bentonite. In one embodiment, inventive system 100 contains approximately between 0-90% by mass first dry reactant 40A, approximately between 0-90% by mass second dry reactant 40B, approximately between 0-40% by mass inorganic coagulant 304, and approximately between 0-40% by mass organic hydrophilic colloid 312. In another embodiment, system 100 contains approximately between 10-50% by mass of each of the first and second dry reactants 40A, 40B, approximately between by mass 0-40% of inorganic coagulant 304, and approximately between 0-40% by mass of organic hydrophilic colloid 312.

In yet another embodiment, outer pouch 105 of system 100 contains a disinfectant generating device 102 having a first dry reactant and a second dry reactant 40A, 40B, a mixture of at least one inorganic coagulant 304, at least one polymeric coagulant 310, and at least one organic hydrophilic colloid 312 stored outside of and separated from device 102. Alternatively, the mixture of inorganic coagulant 304, polymeric coagulant 310, and organic hydrophilic colloid 312 may be stored inside of compartments 30A, 30B of device 102. In another alternative, any two of inorganic coagulant 304, polymeric coagulant 310, and hydrophilic colloid 312 may be stored inside of device 102 and any one of inorganic coagulant 304, polymeric coagulant 310, and hydrophilic colloid 312 may be stored outside of device 102. In yet another alternative, any one of inorganic coagulant 304, polymeric coagulant 310, and hydrophilic colloid 312 may be stored inside of device 102 and any two of inorganic coagulant 304, polymeric coagulant 310, and hydrophilic colloid 312 may be stored outside of device 102. In one embodiment, inventive system 100 contains approximately between 0-90% by mass first dry reactant 40A, approximately between 0-90% by mass second dry reactant 40B, approximately between 0-50% by mass inorganic coagulant 304, approximately between 0-40% by mass polymeric coagulant 310, and approximately between 0-40% by mass organic hydrophilic colloid 312. In another embodiment, system 100 contains approximately between 10-50% by mass of each of the first and second dry reactants, approximately between 0-40% by mass of the inorganic coagulant 304, approximately between 0-30% by mass polymeric coagulant 310, and approximately between by mass 0-30% organic hydrophilic colloid 312.

Figure 5:
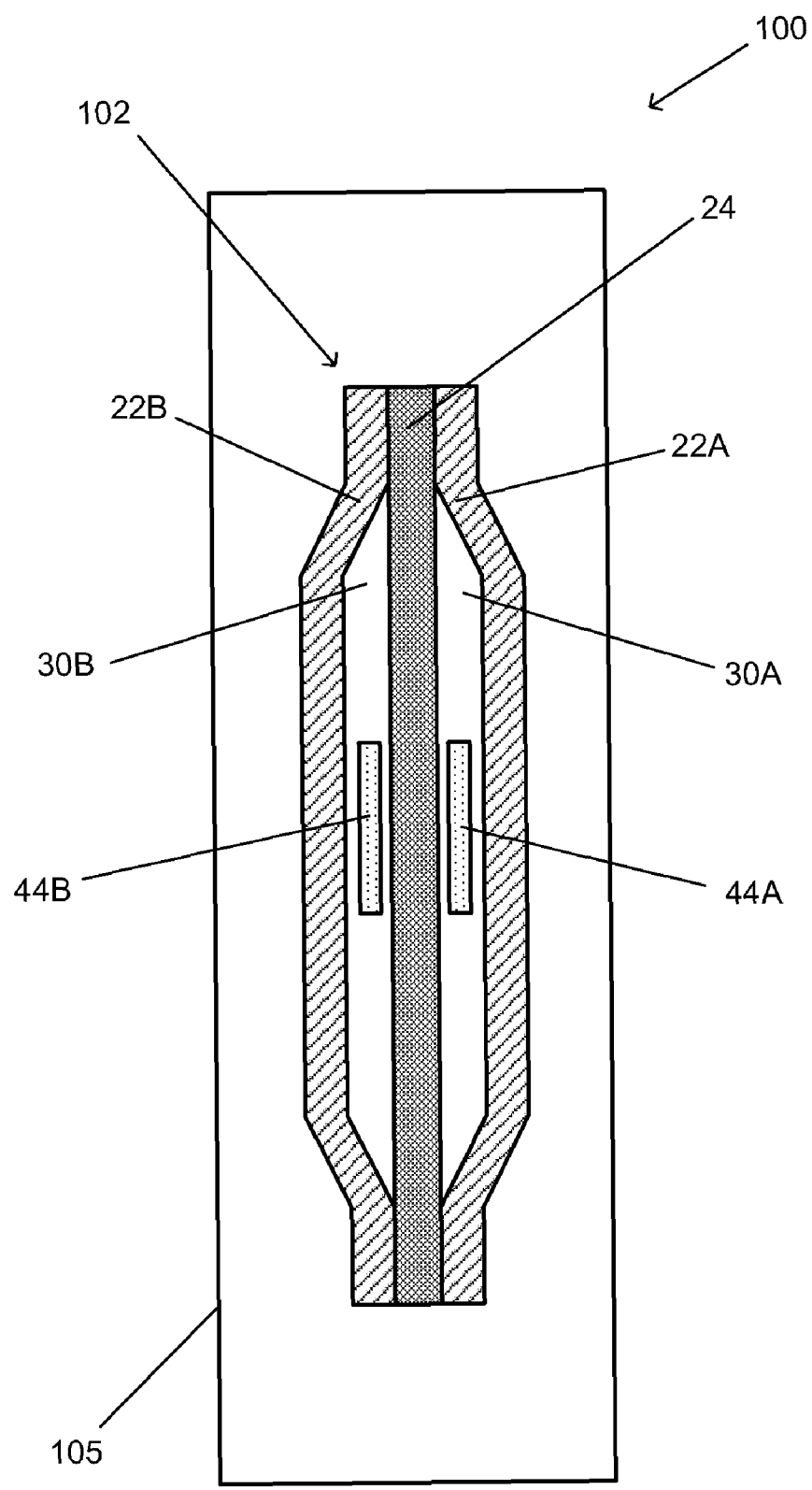
FIG. 5 shows a cross-sectional view of an alternative embodiment of the inventive system, illustrating an outer pouch provided with a disinfectant generating device containing two reactant tablets.
Figure 6:
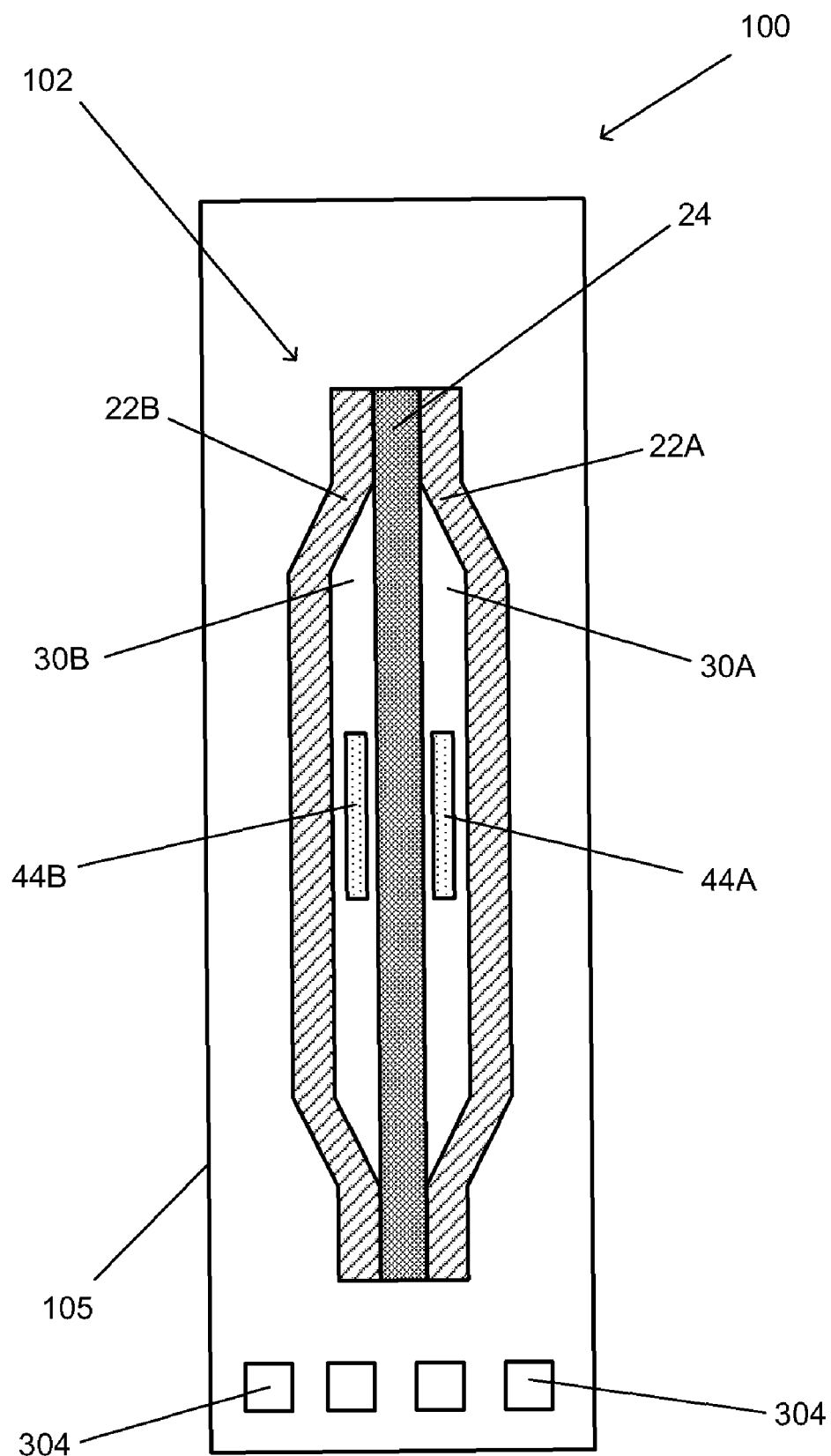
FIG. 6 shows a cross-sectional view of another alternative embodiment of the inventive system, illustrating an outer pouch provided with an inorganic coagulant and a disinfectant generating device containing two reactant tablets and an inorganic coagulant stored outside of the device in the outer pouch.

FIG. 5 shows another embodiment of the inventive system 100 provided with an outer pouch 105 and a disinfectant generating device 102 including a first dry reactant and a second dry reactant in tablet form 44A, 44B. Each tablet 44A, 44B may include at least one inorganic coagulant. Alternatively, powder form of inorganic coagulant may be stored inside of compartments 30A, 30B of disinfectant generating device 102, but separated from tablets 44A and 44B. Still alternatively, as shown in FIG. 6, powder form of inorganic coagulant 304 may be stored in outer pouch 105 and outside of and separated from disinfectant generating device 102.

Figure 7:
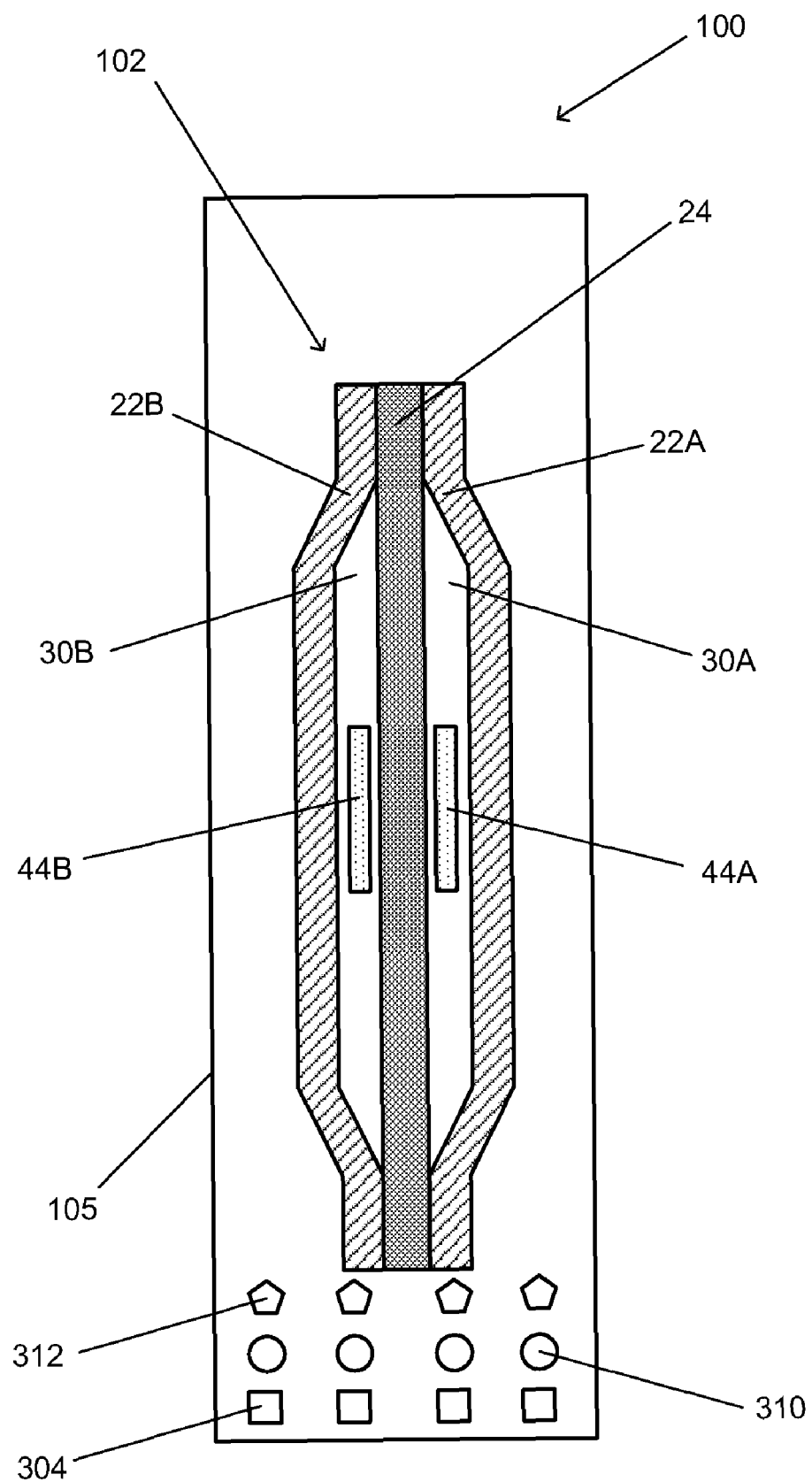
FIG. 7 shows a cross-sectional view of yet another alternative embodiment of the inventive system, illustrating an outer pouch provided with an inorganic coagulant, a polymeric coagulant, an organic hydrophilic colloid, and a disinfectant generating device containing two reactant tablets.

FIG. 7 shows another embodiment of inventive system 100 provided with an outer pouch 105, a disinfectant generating device 102 including a first dry reactant 44A and a second dry reactant 44B in tablet form, and at least one inorganic coagulant 304, at least one polymeric coagulant 310, at least one hydrophilic colloid 312, or any combinations thereof, in powder form, stored outside of and separated from device 102. Alternatively, the powder form of inorganic coagulant 304, polymeric coagulant 310, hydrophilic colloid 312, or any combinations thereof may be stored inside of compartments 30A, 30B of disinfectant generating device 102, but separated from reactant tablets 44A and 44B. In another alternative, tablets 44A and 44B, containing first dry reactant, second dry reactant, inorganic coagulant 304, polymeric coagulant 310, and hydrophilic colloid 312 are stored inside of compartments 30A and 30B of device 102. In yet another alternative, tablets 44A and 44B, containing first dry reactant, second dry reactant, and inorganic coagulant 304 may be stored inside of device, while powder form of polymeric coagulant 310, hydrophilic colloid 312, or combinations thereof may be stored outside of device 102. In still another alternative, tablets 44A and 44B, containing first dry reactant, second dry reactant, and polymeric coagulant 310 may be stored inside of device, while powder form of inorganic coagulant 304, hydrophilic colloid 312, or combinations thereof may be stored outside of device 102. In a further alternative embodiment, tablets 44A and 44B, containing first dry reactant, second dry reactant, and hydrophilic colloid 312 may be stored inside of device, while powder form of inorganic coagulant 304, polymeric coagulant 310, or combinations thereof may be stored outside of device 102.

In yet a further alternative embodiment, tablets 44A and 44B, containing first dry reactant, second dry reactant, and any one, two, or combinations of inorganic coagulant 304, polymeric coagulant 310, and hydrophilic colloid 312 may be stored inside of compartments 30a and 30B of device 102, while powder form of any one, two, or combinations of inorganic coagulant 304, polymeric coagulant 310, and hydrophilic colloid 312 may be stored outside of and separated from device 102.

The disinfectant generating device 102 may include different configurations, e.g., round, triangle, rectangle, parallelogram, trapezoid, diamond, octagon, hexagon, oval, and combinations thereof, to suit different applications. The disinfectant generating device 102 is capable of producing aqueous solutions having antimicrobial and disinfecting properties upon exposure to water and other aqueous solutions. Some examples of antimicrobial and disinfectants include, but are not limited to, chlorine dioxide, peracetic acid, chlorous acid, hydrogen peroxide, bromine, sulfur dioxide, and carbon dioxide.

As shown in FIGS. 1-7, the disinfectant generating device 102 comprises a membrane shell 22 defining at least two compartments 30A, 30B. Each compartment 30A, 30B is provided with an outer membrane 22A and 22B defining walls of device 102. Wick member 24 is provided in connection with membrane shell 22 and extends into one or both compartments 30A and 30B. Each compartment contains at least one dry reactants in stable, solid, and substantially anhydrous powder form 40A, 40B, or tablet form 44A, 44B. These reactants are capable of producing a disinfectant when the device 102 is exposed to water or moisture. The device 102 is preferably exposed to water by placing or submerging it in a container of water.

Referring to FIGS. 1-7, wick member 24 is sealably connected to outer membranes 22A and 22B, dividing disinfectant generating device 102 into two compartments, 30A and 30B. Due to the nature of the membrane employed, wick member 24 functions through capillary action, rapidly absorbing water from outside device 102 and transporting the absorbed water into the compartments 30A and 30B. When dry reactants 40A, 40B stored in compartments 30A and 30B dissolve in the absorbed water and react to produce a disinfectant, the disinfectant efficiently exits compartments 30A and 30B through outer membranes 22A and 22B or through gaps in the seal of the three layers 22A, 22B, and 24, and possibly, to some extent, through wick member 24.

Wick member 24 may be connected to outer membranes 22A and 22B by being directly or indirectly fastened to a portion or all of outer membranes 22A and 22B. Once submerged in water, wick member 24 transports water or solution into the inner compartments 30A and 30B through capillary action. At the same time, a pressure differential between the interior and exterior of the disinfectant generating device 102 causes water to enter device 102 through the gaps in the seals 50A, 50B, 50C, and 50D. As the reaction proceeds, the pressure differential between inside and outside of device 102 equilibrates and the exchange of water and solution slows to eventually reach equilibrium.

As shown by FIGS. 1-7, disinfectant generating device 102 may be defined by two outer membranes 22A and 22B sealed together such that compartments 30A and 30B are formed between the panels. Outer membranes 22A and 22B may be sealed together along a line which extends around the periphery of outer membranes 22A and 22B just inside of the outer edge of device 102. Specifically, the seal extends along line 50A adjacent to the top edge, along line 50B adjacent to the side edge, along line 50C adjacent to the bottom edge, and along line 50D adjacent to the opposite side edge of device 102. Outer membranes 22A and 22B may be sealed together by a variety of means known in the art, including, but not limited to, heat sealing, stitching, heating, and gluing. For example, outer membranes 22A and 22B may be sealed together by means of a heat-sealing device known in the art at regular intervals along lines 50B, 50C, 50D, and continuously along line 50A.

A weight 70 may be inserted in compartments 30A and 30B to ensure that device 102 sinks or is otherwise submerged when placed in a body of water or an aqueous solution. Weight 70 may be attached to device 102 by other means. For example, weight 70 may be attached to or formed as part of membrane shell 22 and/or wick member 24. The size and shape of the weight 70 may vary depending on the size of device 102 in general, the intended application and manufacturing, and packaging concerns. Weight 70 may be formed of a variety of materials such as stainless steel. It is important for the particular material used, however, to be inert with respect to the chemicals in the device. Another method to ensure that device 102 remains submerged in water or an aqueous solution is to place device 102 inside a weighted holder.

In order to reduce the chance of a premature exposure of first dry reactant 40A, second dry reactant 40B, and other chemicals stored in the compartments 30A and 30B to water or moisture, sealed outer membranes 22A and 22B and wick member 24 can optionally be enclosed and sealed in a water-resistant package or protective outer pouch 105.

The shape and size of the panels 22A, 22B, and 24 and corresponding compartments 30A and 30B may vary depending primarily on the amount of chemicals needed for a particular application. Methods for calculating dry reactants needed to produce a given volume and concentrations of a solution having disinfecting properties are known to those skilled in the art. Additional factors affecting the size and shape of the panels 22A and 22B and disinfectant generating device 102 in general include the type of material used to form the panels, the intended application, packaging concerns, and material compatibility. The panels 22A and 22B are preferably square or rectangular in shape in order to facilitate the step of fastening (e.g., sealing) the panels together.

Outer membranes 22A and 22B are formed of a material and put together such that they function as semi-permeable membranes. Outer membranes 22A and 22B must be permeable to the disinfectant. In one embodiment, outer membranes 22A and 22B are substantially impervious (most preferably completely impervious) to liquid (e.g., water). Impervious outer membrane 22A and 22B also protect the dry reactant contents of compartments 30A and 30B so that should small amounts of water inadvertently enter the sealed outer pouch 105 and encounter device 102, the impervious membrane shell 22 will not allow the water to enter compartments 30A or 30B and cause premature reaction of the reactants therein.

Wick member 24 also provides a physical barrier to prevent the contents 40A and 40B of inner compartments 30A and 30B from mixing together. However, because wick member 24 is hydrophilic, the reactants may cross this barrier once they are in dissolved form.

In use, water or another aqueous solution enters device 102 through the capillary action of the wick member 24 or through the gaps in the sides of the fastened membrane shell 22 formed by intermittent fastening (preferably by intermittent heat sealing at regular intervals along lines 50B, 50C, and 50D at the edges of the membrane shell 22). The water or solution enters inner compartments 30A and 30B and dissolves the dry reactants 40A and 40B contained in these spaces. Once in aqueous form, the dissolved reactants 40A and 40B, contained in inner compartments 30A and 30B, may then cross the hydrophilic wick member 24 and contact each other. When the reactants 40A and 40B come into contact, they react and form a disinfectant. The disinfectant generated in compartments 30A and 30B exits the device through outer membranes 22A and 22B, gaps that may be present in the fastened sides, and possibly, to some extent, through the wick member 24.

Disinfectant generating device 102 provides a small, enclosed space in which the conversion of this reaction is enhanced. Outer membranes 22A and 22B are preferably impervious to water to retain dissolved un-reacted chemical in solution inside device 102. The pressure required for the disinfectant to exit compartments 30A and 30B reduces the amount of dissolved, un-reacted chemicals exiting device 102 before being converted to disinfectant. However, gaseous disinfectant such as chlorine dioxide can easily exit the device through the gaps on the sides of device 102. The small volume of compartments 30A and 30B creates an environment with high concentrations of both dissolved reactants 40A and 40B, increasing the chance that the two molecules will come into contact, react, and create the desired disinfectant. Such a setup is desirable in applications wherein the amount of disinfectant generated is critical and needs to be precisely controlled.

In another embodiment, outer membranes 22A and 22B are permeable to liquid and gas. In this embodiment, water can enter the device through outer membranes 22A and 22B and aqueous disinfectant solution formed in device 102 can exit device 102 by way of outer membranes 22A and 22B. This decreases the amount of time required for the desired disinfectant to be generated and is desirable in applications wherein the level of activation is low and immediate use of the solution is desired.

The permeability of outer membranes 22A and 22B with respect to gas and/or water can be the same or not the same depending on the desired function of device 102. For example, outer membrane 22A allows water to pass into one compartment 30A while the outer membrane 22B does not allow water to pass into the compartment 30B.

The selected permeability of outer membranes 22A and 22B with respect to gas and liquid is initially a function of the material composite and can be modified by mechanically, chemically, and/or structurally altering the material. For example, as described below, a plurality of small openings may be formed in one or both of outer membranes 22A and 22B to facilitate the passage of liquid into and out of compartments 30A and 30B. Also, one or both of outer membranes 22A and 22B may be coated with various materials to alter the permeability thereof.

Outer membranes 22A and 22B may be constructed of any membrane material that allows the outer membranes to function as described above; e.g., that allows the membrane shell to be substantially impervious to water but permeable to gas. For example, outer membranes 22A and 22B may be constructed of fibers. The fibers can be hydrophilic, hydrophobic, or any combination thereof. The fibers can be naturally occurring and/or synthetic, and can be woven or non-woven. Additionally, the fibers may be coated or non-coated. For example, the fibers can be coated to seal the fibers to each other or to other materials such as in a laminate composite.

Suitable synthetic fibers for outer membranes 22A and 22B of disinfectant generating device 102 may include, but are not limited to, polyvinyl chloride, polyvinyl fluoride, polytetrafluoroethylene, polyvinylidene chloride, polyacrylics such as Orlon® polyvinyl acetate, polyethylvinyl acetate, non-soluble or soluble polyvinyl alcohol, polyolefins such as polyethylene and polypropylene, polyamides such as nylon, polyesters such as Dacron® or Kodel® polyurethanes, polystyrenes and the like.

The shape and size of the wick member 24 can vary depending on the size of the compartments 30A and 30B, the water absorption rate desired, the type of material used to form the wick member, the intended application, packaging concerns and material compatibility. In the preferable embodiment shown in FIGS. 1-7, the wick member 24 is as wide and extends to the bottom of the compartment 30, forming two compartments the full length and width of the membrane shell, 30A and 30B. These features allow the wick member 24 to absorb and transport a relatively large amount of water on a relatively rapid basis. In order to increase the surface area of the wick member 24 to be exposed to the water even further, for example, the bottom or top ends of the wick member can also extend beyond the outer edge 40 of the disinfectant generating device 102. The wick member 24 is sealed to the panels 22A and 22B around all of its edges, to prevent commingling of the chemicals.

In an application where a relatively slow release of disinfectant is desired, the wick member 24 can be formed of a material that has a relatively slower wicking rate such that water is transported more slowly into the compartment 30.

The wick member 24 can be made out of a large variety of materials. For example, the wick member can be made of virtually any material that features capillary action when in contact with liquid. The wick material thus must be capable of quickly absorbing water and transporting the absorbed water into the device. For example, the material used to form the wick member 24 may be made of synthetic fibers, naturally occurring fiber(s) (both modified and unmodified) or both. The fibers can include hydrophilic fibers, hydrophobic fibers or a combination of hydrophilic and hydrophobic fibers.

Examples of suitable natural fibers for the wick member 24 include cotton, Esparto grass, bagasse, hemp, flax, silk, wool, wood pulp, chemically modified wood pulp, jute, rayon, ethyl cellulose, and cellulose acetate. Suitable synthetic fibers can be made from polyvinyl chloride, polyvinyl fluoride, polytetrafluoroethylene, polyvinylidene chloride, polyacrylics such as Orlon®, polyvinyl acetate, polyethylvinyl acetate, non-soluble and soluble polyvinyl alcohols, polyolefins such as polyethylene and polypropylene, polyamides such as nylon, polyesters such as Dacron® and Kodel®, polyurethanes, polystyrenes and the like. Combinations of natural and synthetic fibers can also be used for the wick member 24, such as Sontara®. In order to function as a wick, certain synthetic fibers may require some modification (e.g., formed into laminates, etc.). The desired wicking action can result form absorption of water, capillary action and/or other mechanisms.

Figure 11:
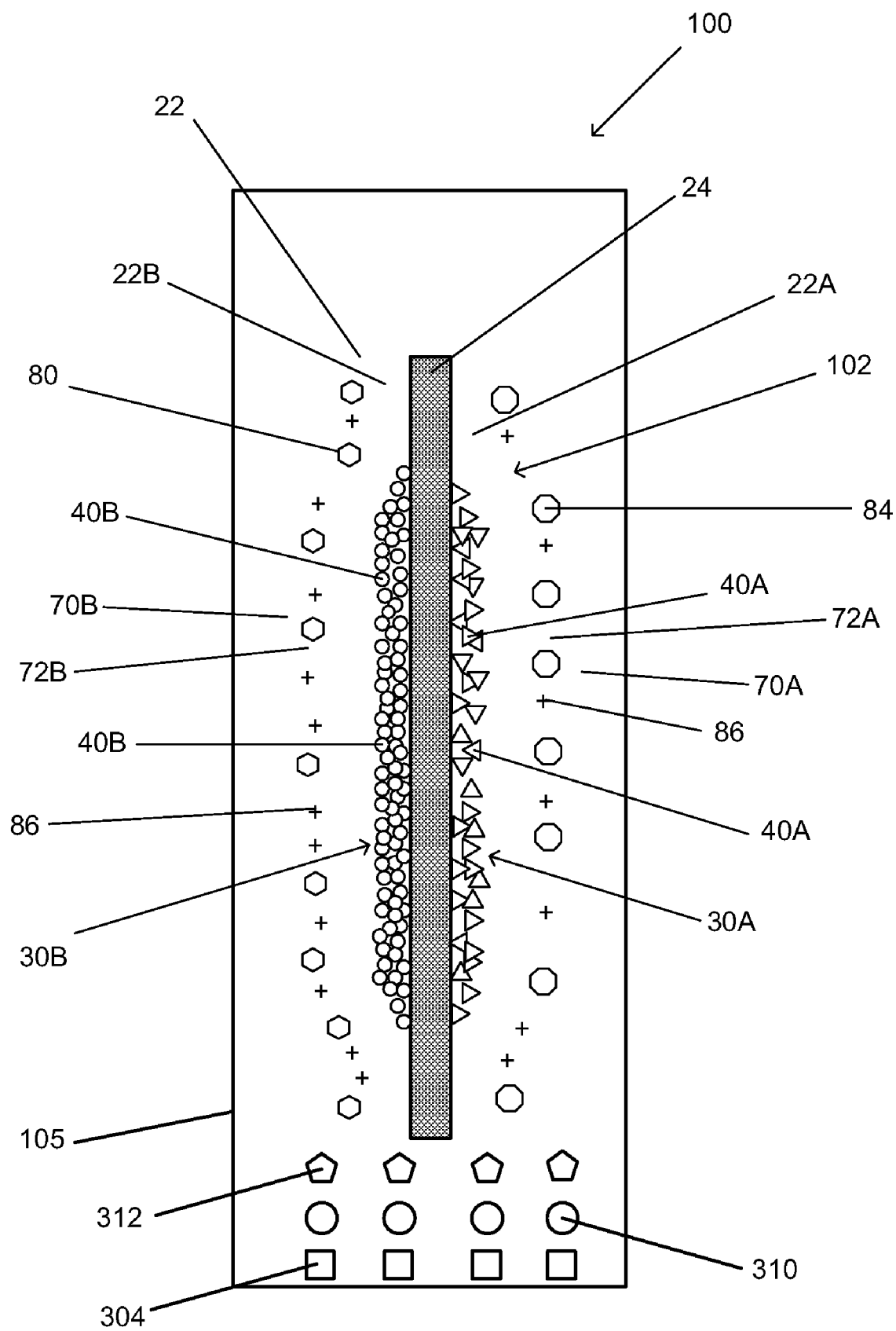
FIG. 11 shows a cross-sectional view of another further embodiment of the inventive system, illustrating an outer pouch provided with an inorganic coagulant, a polymeric coagulant, a hydrophilic colloid, and a disinfectant generating device containing two dry reactants and being provided with two water soluble membranes sealed to the outer membranes of the device, forming outer compartments that contain a surfactant, a fragrance material, and an additive.
Figure 12:
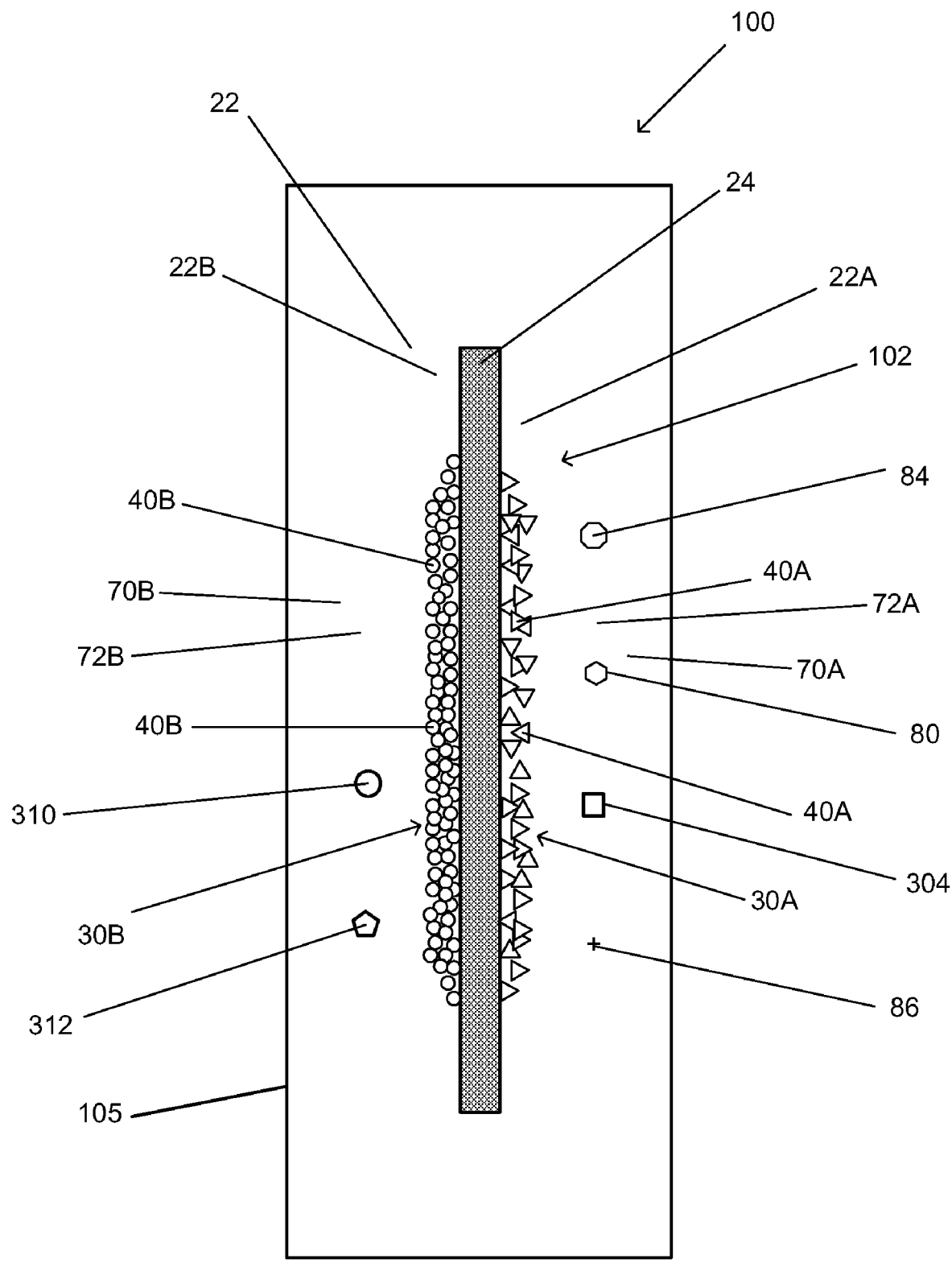
FIG. 12 shows a cross-sectional view of the device shown in FIG. 11, illustrating outer compartments provided with an inorganic coagulant, a polymeric coagulant, a hydrophilic colloid, a surfactant, a fragrance material, an additive.

As shown in FIGS. 11 and 12, the inventive system 100 may be provided with an outer pouch 105 and a disinfectant generating device 102 further provided with at least one water soluble membrane 70A, 70B known in the art, may include, but is not limited to, polyvinyl alcohol, microporous non-woven hydrophobic polymer sheet materials such as non-woven polyethylene (e.g., Tyvek® materials sold by E.I. Du Pont de Nemours & Co.), microporous non-woven polypropylene materials, expanded polytetrafluoroethylene (e.g., GoreTex® sold by W. L. Gore), and kraft paper (e.g., X-Crepe-N Grade 4502 sold by Oliver Products Co.), gelatin, cellulose, and cellulose derivatives such as hydroxypropyl methyl cellulose.

Water soluble membrane 70A, 70B may be sealed substantially continuously to outer membranes 22A, 22B along the edges of the device 102, for example, using a mechanical heat-sealing process, to form a third compartment 72A of device 102. Alternatively, device 102 may additionally be provided with at least two water soluble membranes 70A, 70B and each of the at least two water soluble membranes 70A, 70B is sealed substantially continuously to one of the outer membranes 22A, 22B of the device at the edges to form a third compartment 72A and a fourth compartment 72B of device 102. The third compartment 72A and the fourth compartment 72B may each contain at least one inorganic coagulant 304, at least one polymeric coagulant 310, at least one organic hydrophilic colloid 312, at least one surfactant 80, at least one fragrance material 84, at least one additive 86, or combinations thereof.

Surfactant 80 of the inventive system 100 is capable of cleaning or removing soil from a surface or an aqueous solution, as well as reducing the surface tension of an aqueous solution treated by the inventive system and having disinfectant properties. A lowered surface tension would allow an aqueous solution treated by the inventive system and having disinfectant properties to enter into cracks or pores of a surface, where dirt particles can accumulate. Surfactant 80 may include, but is not limited to, anionic surfactant such as linear alkylbenzene sulfonate, alcohol ethyoxysulfates, alkyl sulfate, nonionic surfactant such as alcohol ethoxylate, cationic surfactant such as quaternary ammonium compounds, amphoteric surfactants such as imidazoline and betaines.

Fragrance materials 84 may be in crystalline form and may include, but are not limited to, linalyl formate and isoamyl acetate.

Additives 86 that contribute to the stability of an aqueous solution treated by the inventive system and having disinfectant properties may include, but is not limited to, suds stabilizers such as alkylamine oxides, suds suppressors such as alkyl phosphates, antiredeposition agents such as polycarbonates and polyethylene, colorants such as pigments and dyes, corrosion inhibitors such as sodium silicate, opacifiers such as titanium dioxide and polymers, processing aids such as clays and polymers, precipitating agents such as sodium carbonate and sodium silicate, ion exchange builders such as zeolites, and sequestrants and chelating agents such as sodium citrate, tetrasodium editronate, EDTA, inorganic phosphates such as trisodium phosphate, detergent and water softener, sodium hexametaphosphate, stabilizer, sequestrant, corrosion inhibitor, scale inhibitor, sodium pyrophosphate, buffer, detergent, and scale inhibitor, and organic phosphates having scale inhibiting, sequestering, deflocculation, and suspended solids dispersing properties such as 1-Hydroxy ethylidene 1,1-diphosphonic acid (HEDP), amino tri-methylene phosphonic acid (ATMP), hexamethylenediamine tetra methylene phosphonic acid, diethylene triamine penta methylene phosphonic acid, bis-hexamethylene triamine penta methylene phosphonic acid, 2-phosphobutane-1,2,4-tricarboxylic acid, homopolymer of maleic acid, carboxymethyl inulin, and 2-Hydroxyethyliminobis methylene phosphonic acid.

In the embodiments of the inventive system as shown in FIGS. 11 and 12, outer pouch 105 may be provided with disinfectant generating device 102 having a first dry reactant and a second dry reactant in powder form 40A, 40B or tablet form 44A, 44B stored in compartments 30A and 30B of device 102. Powder form or tablet form of at least one inorganic coagulant 304, at least one polymeric coagulant 310, at least one organic hydrophilic colloid 312, at least one surfactant 80, at least one fragrance material 84, at least one additive 86, or any combinations thereof may be stored outside of and separated from device 102. Alternatively, powder form or tablet form of inorganic coagulant 304, polymeric coagulant 310, organic hydrophilic colloid 312, surfactant 80, fragrance material 84, additive 86, or any combinations thereof may be stored inside of compartments 72A and 72B of disinfectant generating device 102. In another alternative, powder form or tablet form of inorganic coagulant 304, polymeric coagulant 310, organic hydrophilic colloid 312, or any combinations thereof may be stored in compartments 30A and 30B and powder form or tablet form of surfactant 80, fragrance material 84, additive 86, or any combinations thereof may be stored inside of compartments 72A and 72B or outside of and separated from device 102. In yet another alternative, powder form or tablet form of inorganic coagulant 304, polymeric coagulant 310, organic hydrophilic colloid 312, or any combinations thereof may be stored in compartments 72A and 72B and powder form or tablet form of surfactant 80, fragrance material 84, additive 86, or any combinations thereof may be stored outside of device 102. In still another alternative, any one, two, or combinations of powder form or tablet form of inorganic coagulant 304, polymeric coagulant 310, or organic hydrophilic colloid 312 may be stored in compartments 30A and 30B, and any one, two, or combinations of inorganic coagulant 304, polymeric coagulant 310, and organic hydrophilic colloid 312 in powder form or tablet form, as well as a combination mixture of surfactant 80, fragrance material 84, additive 86, or any combinations thereof, in powder form or tablet form, may be stored outside of device 102 or inside of compartments 72A and 72B.

Figure 8:
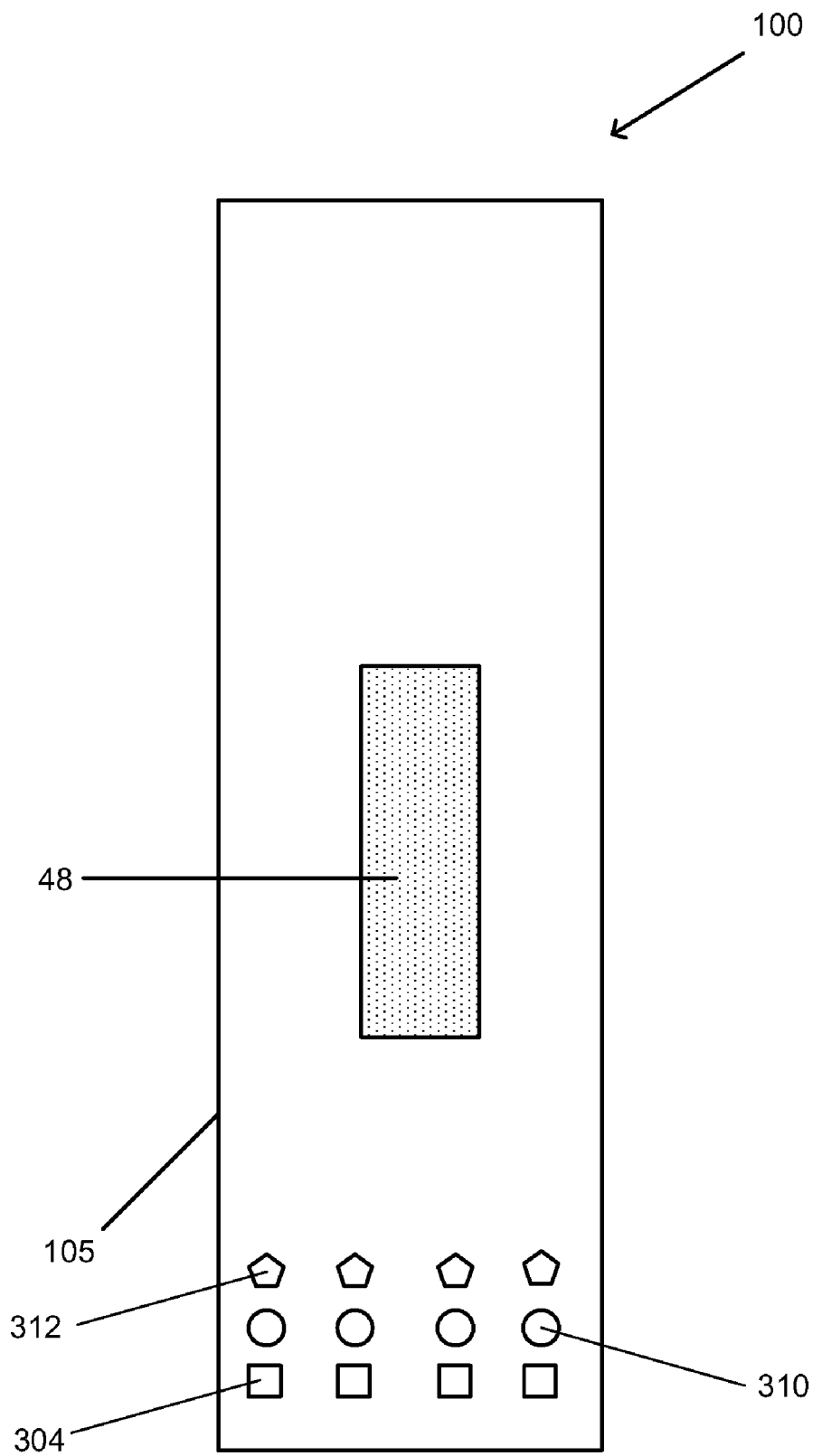
FIG. 8 shows a cross-sectional view of a further embodiment of the inventive system, illustrating an outer pouch provided with a reactant tablet, an inorganic coagulant, a polymeric coagulant, and a hydrophilic colloid.
Figure 9:
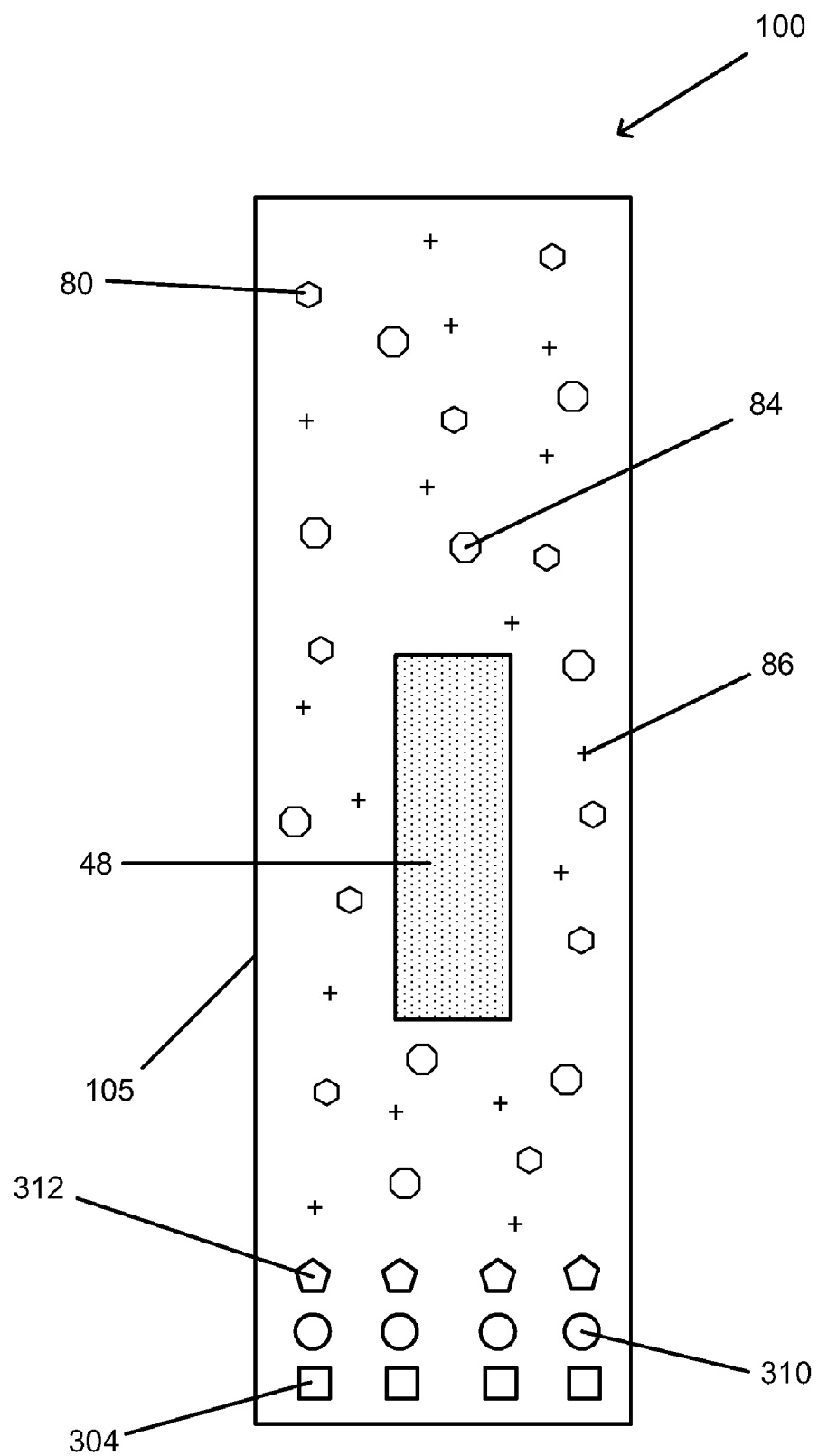
FIG. 9 shows a cross-sectional view of another further embodiment of the inventive system, illustrating an outer pouch provided with a reactant tablet an inorganic coagulant, a polymeric coagulant, a hydrophilic colloid, a surfactant, a fragrance material, and an additive.
Figure 10:
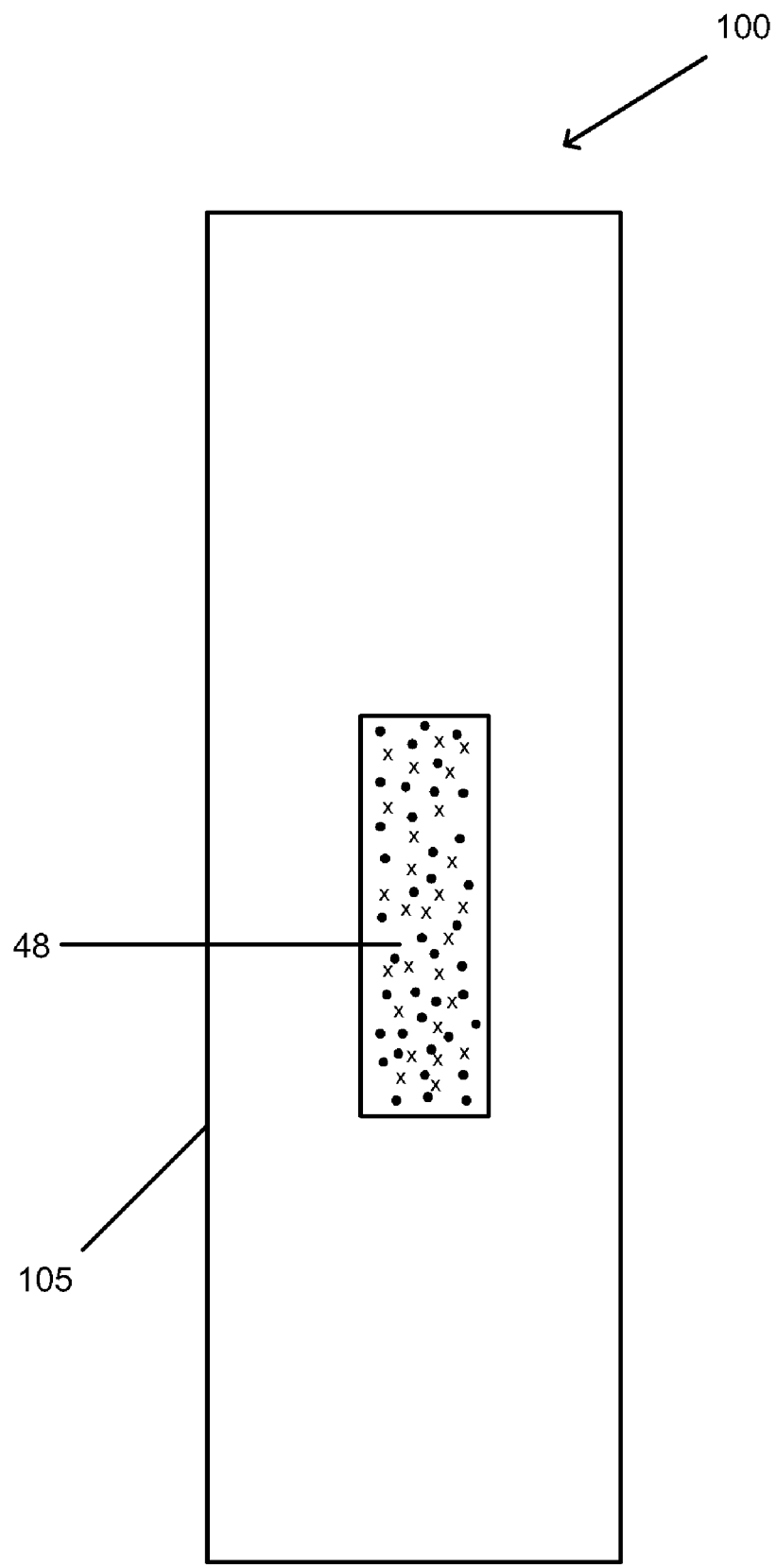
FIG. 10 shows a cross-sectional view of yet another further embodiment of the inventive system, illustrating an outer pouch provided with a reactant tablet.

As shown in FIGS. 8-10, inventive system 100 may be provided with a package comprising a protective outer pouch 105 and at least one tablet 48 having disinfectant properties being stored within outer pouch 105. In one embodiment, inventive system 100 may be provided with an outer pouch 105 including disinfectant tablet 48 that contains at least two dry reactants and at least one inorganic coagulant 304. In another embodiment, inventive system 100 may be provided with an outer pouch 105 including disinfectant tablet 48 that contains at least two dry reactants and at least one inorganic coagulant 304, and additionally at least one polymeric coagulant 310, at least one organic hydrophilic colloid 312, at least one surfactant 80, at least one fragrance material 84, at least one additive 86, or any combinations thereof. Alternatively, any one or any combination of inorganic coagulant 304, polymeric coagulant 310, organic hydrophilic colloid 312, surfactant 80, fragrance material 84, and additive 86 may be stored in outer pouch 105 in powder form, separated from tablet 48 that includes at least two dry reactants. Tablet 48 may be removed from outer pouch 105 and submerged in water or aqueous solutions upon use for generating a disinfectant and substantially eliminating impurities in water or aqueous solutions. Alternatively, the outer pouch may be constructed of a water soluble material and the entire package may be submerged in water or aqueous solutions upon use.

In another embodiment of the inventive system, outer pouch 105 of inventive system 100 may include at least two disinfectant generating tablets 48 and each tablet 48 contains at least one dry reactant, as described above, for the production of a disinfectant. In the alternative, each tablet 48 additionally includes at least one inorganic coagulant 304. In another alternative, each tablet 48 includes at least one dry reactant and at least one inorganic coagulant 304, and additionally at least one polymeric coagulant 310, at least one organic hydrophilic colloid 312, at least one surfactant 80, at least one fragrance material 84, at least one an additive 86, or combinations thereof.

In operation, the elements of the inventive system 100 are immersed in and added into water or an aqueous solution to disinfect and remove solid impurities from the solution. As mentioned above, the disinfectant generating device 102 serves to substantially eliminate microbial contaminants in the solution; the inorganic coagulant 304 promotes aggregation of the solid impurities to form floes; the polymeric coagulant 310 and organic hydrophilic colloid 312 aid in flocculation and clarification of the solution; and the surfactant helps the removal of soil from a solution or a surface and the reduction of surface tension of a cleaning solution. In general, the greater the molecular weight of the polymeric coagulant, the greater the flocculating ability. The longer chain length of the polymeric coagulant allows bridging of flocs. Hydrophilic colloids have an affinity for water molecules and can increase the viscosity of an aqueous solution, thereby improving stability of the solution.

In the embodiment where the disinfectant generating device 102 or tablet 48, containing first and second reactants, also contains inorganic coagulant 304, polymeric coagulant 310, organic hydrophilic colloid 312, surfactant 80, fragrance material 84, or additive 86, the disinfection and purification process is commenced by opening outer pouch 105 of system 100 and placing the disinfectant generating device 102 or tablet 48, including inorganic coagulant 304, polymeric coagulant 310, organic hydrophilic colloid 312, surfactant 80, fragrance material 84, or additive 86, into a vessel, and/or the like, containing a predetermined volume of water or aqueous solution. Depending on what volume of water or aqueous solution is to be treated, the disinfectant generating device is formulated appropriately. For example, the amount of first and second reactants contained in the disinfectant generating device 102 is predetermined to achieve a dose of approximately 1-5 ppm chlorine dioxide in the desired volume of water, ranging from 1 liter to 3800 liters. The presence of coagulant in the product, however, means that lower volumes of water or other aqueous solutions are desirable as the coagulant needs to be stirred into the water. To promote dispersal of disinfectant and the coagulant(s), the aqueous solution is stirred in about 30 seconds intervals for about 30 minutes. The solution is then allowed to settle for about 30 minutes, after which, the solution may be decanted and then filtered, utilizing a filtering device, a towel, or a t-shirt, into clean storage vessels, and the like.

In the embodiment where inorganic coagulant 304, polymeric coagulant 310, organic hydrophilic colloid 312, surfactant 80, fragrance material 84, or additive 86 is stored independently from the disinfectant generating device 102 or tablet 48, inorganic coagulant 304, polymeric coagulant 310, organic hydrophilic colloid 312, surfactant 80, fragrance material 84, or additive 86 is first added into the vessel of water or aqueous solution. The solution is stirred in about 30 seconds intervals for about 30 minutes to allow the formation of flocs. The solution is then allowed to settle for about 30 minutes, after which, the disinfectant generating device 102 or tablet 48 is placed in the solution. The solution is then decanted and filtered similar to the above method.

The inventive system may be used in conjunction with other devices such as, but are not limited to, a storage container such as a vessel of appropriate size with clear markings of volume, and a filtration device.

Figure 13:
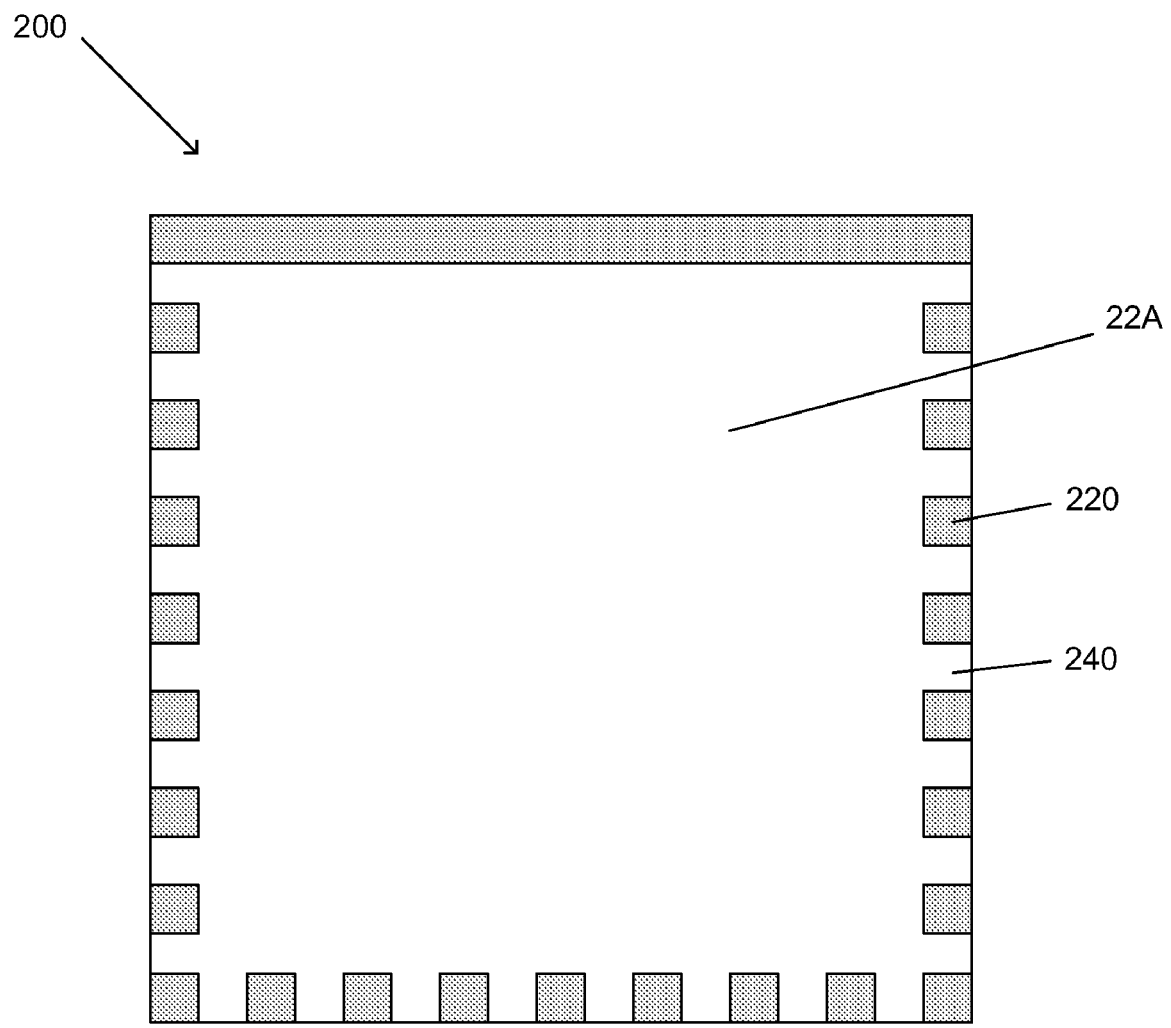
FIG. 13 shows a front elevational view of a disinfectant vapor-generating device having a plurality of small openings along the edges of the device for facilitating passage of moisture into the device.

In another embodiment of the inventive system, as shown in FIG. 13, a disinfectant vapor generating device 200 is provided for producing vapor having disinfectant properties when exposed to ambient moisture. Device 200 is capable of producing disinfecting vapor via a time release manner. In other words, the production of disinfecting vapor may be slow released over a relatively long period of time (weeks to months), or an accelerated release may be provided depending on the construction of the device and arrangement of components. Over time, the release of disinfecting vapor reaches the maximum amount released and then the release levels off and eventually decreases to zero.

Device 200 is provided with an inner membrane that defines and separates a first and a second compartment. These compartments house one or more dry reactants capable of producing disinfecting vapor when the reactants are exposed to ambient moisture. At least two compartments are provided, each having an outer membrane defining walls of the device 200. The outer membrane is moisture and gas permeable; and it is impermeable to liquid water and reactant powders. The inner membrane may be sealed to the outer membranes continuously or non-continuously along the edges of the device 200.

The production of disinfecting vapor via the device 200 is a clear function of relative humidity. The device 200 generates higher amounts of disinfecting vapor at a higher rate of generation when it is placed in an environment with high humidity. In an environment with low humidity, the device 200 produces less disinfecting vapor at a lower rate of generation.

The inner membrane of the device 200 is capable of absorbing and transporting small amounts of partially dissolved reactant across the membrane to the compartment containing the other reactant. The inner membrane also serves to facilitate the transfer of moisture from one compartment to the other. The structure of this inner membrane has unique physical properties. The inner membrane has a high absorbent capacity and absorbency rate in water, oil, and solvents. The inner membrane is preferably hydrophilic, capable of transmitting air or gases (e.g. Frazier porosity>10 $ft^3/ft^2$ min). The inner membrane is preferably also ultra strong, durable, abrasion resistant (e.g. able to withstand tensile strength of 15-30 lbs) and chemically resistant. It is important that the inner membrane is chemically resistant in dry and/or wet conditions in the presence of acidic and/or oxidizing environments, so that the membrane is not degraded or ruptured during placement or operation. The inner membrane is generally made of non-woven materials, preferably made of material generated from a spun lacing process (e.g. hydro entangling process). Materials produced from this process have high absorbent capacities and absorbency rates in water, oil, and solvents. In addition, the materials are ultra strong, durable, and abrasion resistant.

In one embodiment of device 200, the outer membranes and the inner membrane are sealed together continuously along four edges of the device, forming a pouch with a first inner compartment and a second inner compartment. The compartments are provided with dry reactant components capable of producing disinfectant vapor when the reactants react with ambient moisture. The compartments may optionally be provided with additives 86 such as fragrance materials, catalyst, adhesive, thickeners, penetrating agents, stabilizers, surfactants, binders, organic solids, inorganic solids, catalysts, desiccants, deliquescent materials such as potassium sulphate, calcium sulphate, ammonium sulphate, anhydrous sodium sulfate, sodium phosphate, magnesium nitrate, calcium nitrate, magnesium acetate, barium chloride, magnesium chloride, aluminum chloride, calcium chloride, lithium chloride, sodium chloride, potassium chloride, ammonium chloride, potassium bromide, potassium carbonate, sodium carbonate, sodium nitrite, and mixtures thereof.

Deliquescent materials have a strong affinity for moisture and can be used to facilitate transfer of moisture into device 200. For example, in addition to the first and second dry reactant, the first compartment, the second compartment, or the first and second compartments of device 200 may be provided with a deliquescent material, as described above, to facilitate the transfer of moisture into device 200 for the production of a disinfectant vapor.

When the device 200 is exposed to the environment, the moisture in the air naturally penetrates the two outer membranes. As the moisture reaches the compartment, and the reactants become hydrated and slowly become partially dissolved adjacent to the inner membrane. The partially dissolved reactants then come in contact with each other via the inner membrane to produce a disinfectant vapor. Eventually, the generated disinfectant vapor slowly diffuses out of the outer membranes into the surrounding environment.

The outer membranes of device 200 may be constructed from any membrane material that allows the membranes to function as a physical barrier that separate the dry reactants from the environment but are permeable to ambient moisture. The outer membranes are substantially impervious to water and reactant powders but permeable to ambient moisture and disinfectant vapor. The outer membrane materials may be naturally occurring, synthetic, woven, non-woven, or hydrophobic. Additionally, the materials may be coated or non-coated, and may be multi-layered. It is important that the outer membrane has a small mean flow pore size and bubble point (e.g. <10 microns) and low water permeability, so that it is impervious to water while allowing moisture, air and gases to pass through (e.g., Gurley Hill Porosity of 22 seconds/100 cc). In addition, the outer membrane preferably has high tensile strength and pressure, and is chemically resistant. Some examples of suitable synthetic materials for the outer membranes may include, but are not limited to: polyvinyl chloride, polyvinyl fluoride, polyvinylidene chloride, polytetrafluoroethylene, polyacrylics such as Orlon®, polyvinyl acetate, polyethylvinyl acetate, non-soluble or soluble polyvinyl alcohol, polyolefins such as polyethylene and polypropylene, polyamides such as nylon, polyesters such as Dacron® or Kodel®, polyurethanes, polystyrenes, and the like. The outer membranes may also be constructed from: micro porous non-woven polyethylene polymer sheet materials (e.g., Tyvek® brand material sold by Dupont), micro porous non-woven polypropylene materials, expanded polytetrafluoroethylene (e.g., Gore-Tex® brand sold by W. L. Gore), and Kraft paper (e.g., X-Crepe-N Grade 4502 sold by Oliver Products Co.), and the like.

The material of the inner membrane may comprise hydrophilic materials or a combination of hydrophilic and hydrophobic materials that exhibit hydrophilic properties. For example, the inner membrane may be constructed from virtually any material is capable of absorbing moisture/water and transporting the absorbed moisture/water from one compartment to another. Examples of suitable natural materials for the inner membrane include, but are not limited to: cotton, Esparto grass, bagasse, hemp, flax, silk, wool, wood pulp, reactantly modified wood pulp, jute, rayon, ethyl cellulose, and cellulose acetate, and the like. Suitable synthetic materials for the inner membrane may include, but are not limited to: polyvinyl chloride, polyvinyl fluoride, polytetrafluoroethylene, polyvinylidene chloride, polyacrylics such as Orlon®, polyvinyl acetate, polyethylvinyl acetate, non-soluble and soluble polyvinyl alcohol, polyolefins such as polyethylene and polypropylene, polyamides such as nylon, polyesters such as Dacron® or Kodel®, polyurethanes, polystyrenes, and the like. In addition, the materials may be made of the combination of natural materials and synthetic materials that are derived from non-woven technologies. One preferred process for producing non-woven materials is a spun lacing process (hydro entangling process). Materials produced by this process contain no binders or glues, are low-linting, have high texture-like and high absorbent capacity and absorbency rates in water, oil and solvents. In addition, they are ultra strong, durable, and abrasion resistant. Examples of these materials are Sontara® engineered-cloth wipers produced by Dupont® (Sontara® AC™, Sontara® SPS™, Sontara® FS™, Sontara® EC™, Sontara® ERC™, Sontara® PC™).

In another embodiment of device 200, as shown in FIG. 13, the two outer membranes and inner membrane may be mechanically heat-sealed together non-continuously along three edges of the device 200 to form a pouch with a plurality of small openings 240 distributed around the three edges for facilitating moisture into the device 200. Along one edge of the device 200, the membranes are sealed together continuously, without the small openings 240. As shown in FIG. 13, area 220 is the area where the membranes are mechanically heat-sealed together; whereas, area 240 is the area where the membranes are not mechanically heat-sealed together, but rather, the membranes are mechanically compressed. The small openings 240 are sealed in a way such that the dry reactant components can remain inside of the device 200. These small openings 240 increase the moisture transfer rate into the device 200, the reactants' dissolution rate, the disinfectant generation rate, and the facilitation rate of disinfectant vapor out of the device 200. Device 200 may be designed in such a way that the number of small openings on the edges of the device may vary, depending on the desired disinfectant vapor production rate.

In the embodiment as shown in FIG. 13, when the inner membrane of device 200 is constructed from materials capable of absorbing water and moisture, the device 200 is capable of transporting water into the device 200 through the wicking effect of the inner membrane. The transportation of a small amount of water into the device 200 through compressed areas 240 on the edges of the device 200 significantly shortens the time required for disinfectant vapor to be produced, which may function as a device for fast-release of disinfectant vapor.

First and second dry reactants utilized in connection with the inventive system may be in any dry physical form. Examples of the dry physical form include, but are not limited to: powders, granules, pellets, tablets, agglomerates, and the like. Preferably, the components are in powder form because powders have a larger surface area, and tend to dissolve in water and react more quickly when compared to large particles, such as pellets or agglomerates.

First dry reactant 40A and second dry reactant 40B capable of producing a disinfectant upon exposure to water or moisture may be a metal chlorite component and an acid component. As the water or moisture is wicked into the membrane shell through capillary action and reaches, for example, the metal chlorite component 40A and acid component 40B, the components 40A and 40B become hydrated and slowly become partially dissolved adjacent in compartments 30A and 30B, adjacent to the wick member 24. The partially dissolved reactants 40A and 40B then can cross the hydrophilic wick membrane 24 and contact each other to produce chlorine dioxide inside the pouch by the following reactant reaction: $5 ClO_2^- + 5 H^+ \rightarrow 4 ClO_2 + HCl + 2 H_2O$. Eventually, the generated chlorine dioxide slowly diffuses out of the membrane shell 22 into the surrounding environment.

For the production of chlorine dioxide, the metal chlorite component may comprise sodium chlorite, particularly dry technical grade sodium chlorite (containing about 80% by weight sodium chlorite and 20% by weight of sodium chloride, sodium chlorate and others), calcium chlorite, potassium chlorite, barium chlorite, magnesium chlorite, alkali metal chlorites, alkaline earth metal chlorites, and mixtures thereof.

Generally, a dry solid hydrophilic acid component is employed, which does not substantially react with the metal chlorite component until the reactants are partially dissolved and come in contact by crossing through hydrophilic wick member 24. Examples of acid components that may be used in the production of chlorine dioxide include, but are not limited to, sodium bisulphate, citric acid, mandelic acid, boric acid, lactic acid, tartaric acid, maleic acid, malic acid, glutaric acid, adipic acid, acetic acid, formic acid, sulfamic acid, sulfuric acid, hydrochloric acid, phosphoric acid, phosphoric anhydride, sulfuric anhydride, water soluble organic acid anhydrides, such as maleic anhydride, and water soluble acid salts, such as calcium chloride, magnesium chloride, magnesium nitrate, lithium chloride, magnesium sulfate, aluminum sulfate, sodium acid sulfate, sodium dihydrogen phosphate, potassium acid sulfate, potassium dihydrogen phosphate, and mixtures thereof.

When disinfectant generating device 102 contains sodium chlorite as a metal chlorite component and sodium persulfate as second dry reactant, the device 102, upon exposure to water or moisture, is capable of producing chlorine dioxide via oxidation of sodium chlorite by sodium persulfate by the following reaction: $2 NaClO_2 + Na_2S_2O_8 \rightarrow 2 ClO_2 + 2 Na_2SO_4$.

When disinfectant generating device 102 contains sodium chlorite as a metal chlorite component and a chlorine releasing compound as a acid component, the device 102, upon exposure to water or moisture, is capable of producing chlorine dioxide via oxidation of the sodium chlorite by the chlorine releasing compounds by, for example, the following reaction: $2 NaClO_2 + NaClO + HCl \rightarrow 2 ClO_2 + 2 NaCl + NaOH$.

When disinfectant generating device 102 contains sodium chlorate as a metal chlorite component and oxalic acid as a acid component, the device 102, upon to exposure to water, is capable of producing chlorine dioxide via reduction of the sodium chlorate by the oxalic acid by the following reaction: $2 NaClO_3 + H_2C_2O_4 \rightarrow 2 ClO_2 + 2 CO_2 + 2 H_2O$.

In addition to chlorine dioxide, the inventive device 102 may be employed to produce other disinfectants upon exposure to water or moisture. For example, peracetic acid may be produced by the device 102 when first and second dry reactants 40A and 40B, are tetraacetylethylenediamine (TAED) and peroxygen compounds. Peroxygen compounds release hydrogen peroxide, which reacts with TAED to produce peracetic acid and diacetylethylenediamine (DAED) as follows: $TAED + 2 H_2O_2 \rightarrow 2 CH_3COOH + DAED$. Both TAED and DAED are non-toxic and non-sensitizing, and are readily biodegraded in the environment. Examples of peroxygen compounds include, but are not limited to, sodium percarbonate, sodium perborate, and urea hydrogen peroxide.

Bromine may also be produced by the device 102 when first and second dry reactants 40A and 40B are a sodium bromide and a potassium monopersulfate compound. The bromine is produced via the oxidation of sodium bromide by potassium monopersulfate compounds as follows: NaBr+Potassium monopersulfate→Hypobromous acid.

Sulfur dioxide may be produced by the device 102 when first and second dry reactants 40A and 40B are a sodium bisulfite and an acid component. The sulfur dioxide is produced via the activation of sodium bisulfite with the acid: $NaHSO_3 + H^+ \rightarrow SO_2 + Na^+ + H_2O$. Examples of the acid component include, but are not limited to, citric acid and fumaric acid.

Carbon dioxide may be produced by the device 102 when first and second dry reactants 40A and 40B are sodium carbonate and an acid component. The carbon dioxide is produced via the activation of sodium carbonate with the acid: $CaCO_3 + 2\ H^+ \rightarrow CO_2 + H_2O + Ca^+$. The acid component may be, for example, citric acid.

Further, the reactants 40A and 40B may each be impregnated on inert carriers that are reactantly compatible with the reactants 40A and 40B. The coagulants, colloids, surfactants, fragrance materials, and additives also may be impregnated on inert carriers. A carrier is useful to control the release of the reactants 40A and 40B, and thus the reaction may be further controlled. Examples include, but are not limited to: zeolite, kaolin, mica, bentonite, sepiolite, diatomaceous earth synthetic silica, and the like.

The following example is provided to further illustrate the effectiveness of the disinfectant generating device of present invention.

EXAMPLE 1

Two layers of a microporous, hydrophobic non-woven polyethylene sheet material (Tyvek® sold by E.I. Du Pont de Nemours & Co.—type 1073B) was intermittently heat sealed to a hydrophilic material consisting of non-woven natural and synthetic fibers (Sontara® sold by Dupont). The Sontara® was placed between the two layers of Tyvek® and the bottom and sides were sealed forming a pouch divided in two, creating two compartments. The pouch measured 2.5 inches by 2.5 inches. One compartment of the pouch was filled with 0.4 g technical grade sodium chlorite of 80% purity and the other compartment was filled with 0.4 g sodium bisulfate. The pouch was placed in 5 gallons of tap water at 20° C. The absorbance of the solution was measured with a spectrophotometer at a wavelength of 360 nm and then converted to an mg/l concentration of chlorine dioxide.

TABLE 1

| Time | Concentration |
| --- | --- |
| 0 min. | 0 mg/l |
| 15 min. | 2.5 mg/l |
| 30 min. | 3.5 mg/l |
| 45 min. | 3.8 mg/l |
| 60 min. | 3.8 mg/l |

This final concentration of 3.8 mg/l is near the upper bound of chlorine dioxide required to disinfect unclean water. Municipal water treatment plants typically use between 1 and 2.5 ppm chlorine dioxide for disinfection, usually after a clarification and sedimentation process. By changing the masses of the reactants used to manufacture the pouch, the concentration of chlorine dioxide produced in this volume of water can easily be decreased or increased as necessary.

It will be understood that the foregoing descriptions of various embodiments of systems and methods for the present invention are merely illustrative of the invention and its varied embodiments. Modifications to various aspects of the systems and methods of the present invention will be apparent to hose skilled in the art and are intended to fall within the scope and purview of this disclosure and the following claims.

We claim:

1. A device for producing a vapor having disinfecting properties when exposed to ambient moisture, comprising:
    at least two outer membranes permeable to moisture and vapor; and
    at least one inner membrane continuously sealed to the at least two outer membranes along at least one side of the device, and non-continuously sealed along at least one side of the device;
    wherein the outer membranes and the inner membrane together form a first compartment and a second compartment separated by the inner membrane, wherein the first compartment is provided with a first dry reactant and the second compartment is provided with a second dry reactant, and wherein the first dry reactant and the second dry reactant are different, and whereby the vapor having disinfecting properties is generated and released to the atmosphere from the device when the first dry reactant in the first compartment is hydrated by moisture penetrating the outer membranes, and the hydrated first dry reactant is transported across the inner membrane to contact the second dry reactant in the second compartment to generate the vapor having disinfecting properties, and wherein the first dry reactant and the second dry reactant chemically react with each other when hydrated to generate the vapor.

2. The device of claim 1, wherein the first dry reactant and the second dry reactant are in a form selected from the group consisting of: powders, granules, pellets, tablets, agglomerates, and mixtures thereof.

3. The device of claim 1, wherein the first dry reactant is selected from the group consisting of: sodium chlorite, calcium chlorite, potassium chlorite, barium chlorite, magnesium chlorite, alkali metal chlorites, alkaline earth metal chlorites, sodium chlorate, tetraacetylethylenediamine (TAED), sodium bromide, sodium bisulfite, alkali metal chlorites, alkaline earth metal chlorites, and mixtures thereof.

4. The device of claim 1, wherein the second dry reactant is selected from the group consisting of: sodium bisulphate, citric acid, mandelic acid, boric acid, lactic acid, tartaric acid, maleic acid, malic acid, glutaric acid, adipic acid, acetic acid, formic acid, sulfamic acid, sulfuric acid, hydrochloric acid, phosphoric acid, fumaric acid, phosphoric anhydride, sulfuric anhydride, water soluble organic acid anhydrides, maleic anhydride, water soluble acid salts, calcium chloride, magnesium chloride, magnesium nitrate, lithium chloride, magnesium sulfate, aluminum sulfate, sodium acid sulfate, sodium dihydrogen phosphate, potassium acid sulfate, potassium dihydrogen phosphate, sodium persulfate, oxalic acid, peroxygen compounds, sodium percarbonate, sodium perborate, urea hydrogen peroxide, potassium monopersulfate, and mixtures thereof.

5. The device of claim 1, further comprising at least one deliquescent material stored within the first compartment or the second compartment of the device.

6. The device of claim 1, further comprising at least one fragrant additive disposed within at least one of the first compartment and the second compartment.

7. The device of claim 1, wherein the at least one inner membrane is non-continuously sealed to the at least two outer membranes along three sides of the device.

8. The device of claim 7, wherein the at least three non-continuously sealed sides define a plurality of apertures.

9. The device of claim 8, wherein each of the plurality of apertures is sized to be impermeable to the first dry reactant and the second dry reactant.

* * * * *